(12) United States Patent
Segall

(10) Patent No.: US 11,594,151 B2
(45) Date of Patent: Feb. 28, 2023

(54) WEARABLE MEDICAL TRAINING DEVICE

(71) Applicant: Strategic Operations, Inc., San Diego, CA (US)

(72) Inventor: Stuart C. Segall, La Jolla, CA (US)

(*) Notice: Subject to any disclaimer, the term of this patent is extended or adjusted under 35 U.S.C. 154(b) by 215 days.

(21) Appl. No.: 16/909,273

(22) Filed: Jun. 23, 2020

(65) Prior Publication Data

US 2021/0082318 A1 Mar. 18, 2021

Related U.S. Application Data

(63) Continuation of application No. 15/859,112, filed on Dec. 29, 2017, now Pat. No. 10,726,743.

(51) Int. Cl.
| | |
|---|---|
| *G09B 23/30* | (2006.01) |
| *A61B 17/00* | (2006.01) |
| *A61M 1/00* | (2006.01) |
| *A61F 13/02* | (2006.01) |
| *A61B 17/12* | (2006.01) |

(52) U.S. Cl.
CPC ........ *G09B 23/303* (2013.01); *A61B 17/0057* (2013.01); *A61M 1/90* (2021.05); *G09B 23/30* (2013.01); *A61B 17/12122* (2013.01); *A61F 13/0226* (2013.01); *A61F 13/0276* (2013.01); *A61L 2400/04* (2013.01)

(58) Field of Classification Search
CPC ....... G09B 23/28; G09B 23/30; G09B 23/303
See application file for complete search history.

(56) References Cited

U.S. PATENT DOCUMENTS

| | | | | |
|---|---|---|---|---|
| 3,027,655 | A * | 4/1962 | Alderson | G09B 23/32 434/268 |
| 3,852,893 | A * | 12/1974 | Smrcka | G09B 23/32 264/DIG. 14 |
| 5,839,904 | A * | 11/1998 | Bloom | G09B 23/285 434/272 |
| 8,491,309 | B2 * | 7/2013 | Parry | G09B 23/30 434/272 |
| 8,944,825 | B2 * | 2/2015 | Reid-Searl | G09B 23/30 434/267 |
| 9,142,144 | B2 * | 9/2015 | Meglan | G09B 23/30 |
| 9,342,996 | B2 * | 5/2016 | King | G09B 9/00 |
| 10,360,817 | B2 * | 7/2019 | Segall | G09B 23/28 |
| 10,803,761 | B2 * | 10/2020 | Welch | G06F 3/016 |
| 2013/0224712 | A1 * | 8/2013 | Day | A61K 35/12 434/268 |

(Continued)

*Primary Examiner* — Kurt Fernstrom
(74) *Attorney, Agent, or Firm* — Enrique A. Monteagudo, Esq.

(57) ABSTRACT

The present disclosure, when used by a live actor, may allow users to safely simulate hemorrhaging in some of the most challenging blood vessels in the most challenging anatomical locations such as the carotid artery, the axillary artery, and the femoral artery. The present disclosure may further provide the ability for users to safely perform hemorrhage control procedures, such as compression and ligation. The simulated wound of the present disclosure may be compressed to control hemorrhage. The simulated wound receptacle of the present disclosure may be packed with hemostatic or simple gauze to control hemorrhage. The simulated blood vessel of the device may be ligated with hemostats or other ligating instruments or material and bandaged with pressure dressings to control hemorrhage.

15 Claims, 21 Drawing Sheets

(56) References Cited

U.S. PATENT DOCUMENTS

| | | | |
|---|---|---|---|
| 2013/0309643 A1* | 11/2013 | Segall | G09B 23/303 |
| | | | 434/268 |
| 2015/0221238 A1* | 8/2015 | Huebner | G09B 23/288 |
| | | | 434/262 |
| 2016/0171911 A1* | 6/2016 | Parry, Jr. | G09B 23/30 |
| | | | 434/268 |
| 2017/0193858 A1* | 7/2017 | Segall | G09B 23/303 |
| 2018/0158373 A1* | 6/2018 | Hendrickson | G09B 23/285 |
| 2020/0013314 A1* | 1/2020 | Hare | A41D 13/129 |

* cited by examiner

WEARABLE MEDICAL TRAINING DEVICE

CROSS-REFERENCE TO RELATED APPLICATION

This application is a continuation of currently pending U.S. patent application Ser. No. 15/859,112, filed Dec. 29, 2017 and entitled "multi-junctional bleeding simulator"; which claims the benefit of priority to U.S. provisional patent application No. 62/441,064, filed Dec. 30, 2016 and entitled "multi-junctional bleeding simulator"; all of which are incorporated by reference herein in their entirety.

BACKGROUND OF THE INVENTION

Technical Field

The present disclosure relates generally to casualty simulation and medical response team training systems, such as a wearable medical training device. The present disclosure is more particularly, though not exclusively, a simulated wound apparatus allowing the wearer to simulate injuries for purposes of casualty simulation and medical response training.

Related Art

Hemorrhage is the leading cause of preventable death on the battlefield. For the injured having potentially survivable wounds, ninety percent die from uncontrolled hemorrhage. Some of the most challenging blood vessels are the carotid arteries, the axillary arteries, and the femoral arteries. The carotid arteries supply the head and neck with oxygenated blood. The axillary arteries are large blood vessel that convey oxygenated blood to the lateral aspects of the thorax, each axilla (armpits) and the upper limbs. The femoral arteries are large arteries in the thigh, and the main arterial supply to the thigh and leg. It enters the thigh from behind the inguinal ligament in the inguinal region of the body (also known as the groin) as the continuation of the external iliac artery.

The majority of combat fatalities occur forward of a medical treatment facility. To raise the probability of survival from a bleeding wound so the injured may reach a medical treatment facility, the hemorrhage must be controlled immediately. To stop the bleeding, first responders are taught to find the wound and to stop the bleeding by occluding the blood vessel by compression or ligation. By applying direct pressure to the wound, it is possible the damaged blood vessel may be compressed closed. Alternatively, the damaged blood vessel may be compressed upstream with a tourniquet to cut off blood flow to the damaged blood vessel. Additionally, the wound may be compacted with material to obstruct the damaged blood vessel or the damaged blood vessel may be directly ligated. Under the extreme conditions and pressures of a combat zone, proper training is needed to ensure the correct procedure is performed to stop a hemorrhage and to save a life.

As is well known, and widely accepted, partial task simulators and training aids can be very effective for teaching individuals how to perform a wide variety of different tasks. More specifically, they can be extremely helpful for teaching an individual how to perform certain medical procedures during a life-threatening, emergency situation. In this context, and of particular importance for the present disclosure, are those medical procedures that are required for hemorrhage control in a combat zone. The import here is two-fold. Firstly, the partial task simulator should effectively augment the educational background that is necessary to assess an emergency situation. Secondly, it should serve as a tool with which a person can learn how to respond to an emergency situation by properly performing essential life-saving tasks. The efficacy of any partial task simulator or training aid, however, is dependent on the realism it provides and its ability to simulate or mimic an environment where the task is to be actually performed.

With the above in mind, a catastrophic event presents a situation wherein the proper training of emergency medical personnel can be invaluable. Regardless whether the event is the result of an accident, a natural disaster or some form of combat, the consequence of a first response to the event may make the difference between life and death. In such instances, the ability of medical personnel to rapidly and reliably attend to wounds and injuries is of crucial importance. Practice on partial task simulators such as medical mannequins, while valuable as teaching aids, are limited by the mannequin's immobility, weight, expense and minimal interaction with the medical personnel.

In light of the above, it is an object of the present disclosure to provide a device for realistically and dynamically simulating the wounds and injuries on a person (e.g., role player, actor) that can be received during a traumatic event. Another object of the present disclosure is to provide a device that effectively functions as a training aid to teach a person how to treat the wounds and injuries that can be received by a person during a traumatic event. Another object of the present disclosure is to provide a device that effectively functions as a training aid that allows verbal and gesticular interaction between a live human wearing the device and a first responder who is treating the person wearing the device. Still another object of the present disclosure is to provide a training aid for teaching how to treat wounds and injuries that is easy to use, is simple to manufacture and is comparatively cost effective.

U.S. Pat. No. 10,217,380 issued to Parry et al. on Feb. 26, 2019 shows a wound box trainer applicable to training personnel in the treatment of a traumatic injury is presented. The wound box trainer includes a case, a compressible body, a wound structure, and an annular cavity. The case further includes a base and a lid. The compressible body simulates a portion of a body and further includes a top surface and a bottom surface. The compressible body resides within the base. The wound structure simulates an injury disposed along the compressible body. The wound structure includes a wound cavity which extends into the compressible body. An annular cavity extends into the compressible body about the wound cavity. The annular cavity permits movement and/or expansion of a wall defined by and between the wound cavity and the annular cavity when probed by a finger or instrument and packed with gauze, bandages, and the like during treatment of the wound structure to stem blood lose from a bleed tube. The wound box trainer overcomes identified deficiencies of body worn trainers by virtue of being disposed within a carrying case.

U.S. Pat. No. 5,839,904 issued to Bloom on Nov. 24, 1998 shows a phlebotomy training device including a core member incorporating a network of channels wherein resilient tubing is placed to form artificial veins and arteries. The tubing communicates with a fluid reservoir disposed at a proximal end of the device for maintaining the tubing full of fluid. A membrane covers the device and presents a puncture resistant characteristics similar to that of skin. The device is adapted for attachment to a person's arm so that a student can practice venipuncture techniques on a live subject, including the proper positioning of an actual human arm, without the risks associated with puncturing living tissue.

The present disclosure is directed toward overcoming known problems and problems discovered by the inventor.

SUMMARY OF THE INVENTION

Aspects of the present disclosure generally pertain to towards a wearable medical training device. Aspects of the present disclosure more specifically are directed toward a device for training of hemorrhage control procedures on junctional bleeding.

A wearable medical training device to be worn by a wearer for simulation of junctional bleeding of the wearer is disclosed herein. The wearable medical training device includes a user interface configured to be worn by the wearer proximate a junction of the wearer when worn, a simulated hemorrhaging wound coupled to the user interface and configured to simulate a wound bleeding from said junction, and a blood feed coupled to the user interface and the simulated hemorrhage wound. The blood feed is configured to communicate a simulated blood to the simulated hemorrhaging wound, and further configured to reduce or at least substantially stop a flow of the simulated blood to the simulated hemorrhaging wound upon proper performance of a hemorrhage control procedure.

According to one embodiment, a multi-junctional bleeding simulator to be worn by a wearer for simulation of junctional bleeding of the wearer is also disclosed herein. The multi-junctional bleeding simulator includes a multi-junctional attachment unit, a simulated hemorrhage wound coupled to the multi-junctional attachment unit, and a blood plumbing system coupled to the multi-junctional attachment unit and the simulated hemorrhage wound. The multi-junctional attachment unit is configured to be worn by the wearer proximate a neck junction, repositioned and worn by the wearer proximate an axillary junction of the wearer, and further repositioned and worn by the wearer proximate an inguinal junction. The simulated hemorrhage wound is configured to simulate a junctional bleeding wound and simulated bleeding from said junctional bleeding wound. The blood plumbing system is configured to communicate a simulated blood to the simulated hemorrhage wound, and is further configured to reduce or at least substantially stop a flow of the simulated blood to the simulated hemorrhage wound upon proper performance of a hemorrhage control procedure.

According to one embodiment, a system for training hemorrhage control procedures on a wearer is also disclosed herein. The system includes a pumping system and a wearable medical training device or a multi-junctional bleeding simulator to be worn by the wearer for simulation of junctional bleeding of the wearer, as described above. The pumping system included a supply of a simulated blood, a simulated blood pump configured to transmit the simulated blood, and a simulated blood reservoir configured to receive the simulated blood. The blood plumbing system is hydraulically coupled to the pumping system between the simulated blood pump and the simulated blood reservoir, and is configured to communicate the simulated blood to at least one of the simulated hemorrhage wound and the simulated blood reservoir.

BRIEF DESCRIPTION OF THE DRAWINGS

The nature, objects, and advantages of the present disclosure will become more apparent to those skilled in the art after considering the following detailed description in connection with the accompanying drawings, in which like reference numerals designate like parts throughout, and wherein.

DETAILED DESCRIPTION

Figure 1:
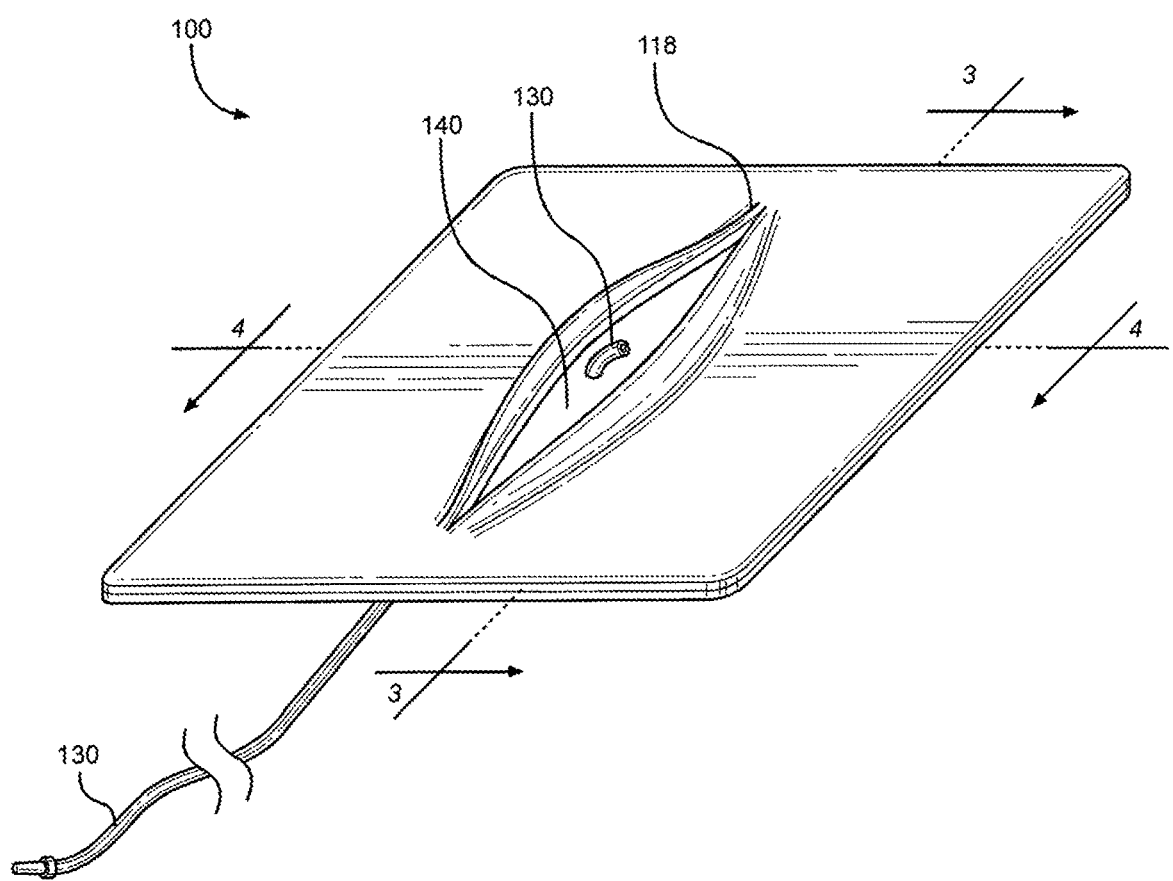
FIG. 1 is a perspective view of a multi-junctional bleeding simulator, showing a simulated wound with a simulated blood vessel, according to one embodiment of the disclosure.

The multi-junctional bleeding simulator of the present disclosure is designed as a wearable medical training device, or more particularly, a human worn partial task hemorrhage control simulator. The wearable medical training device may include a user interface configured to be worn by the wearer proximate a junction of the wearer when worn. In particular, the multi-junctional bleeding simulator may be designed to be worn in at least one of three positions as follows: bilateral anterior-frontal-peracervical ("neck" or "neck junction"), bilateral axillary ("armpit" or "axillary junction"), and bilateral anterior-inguinal ("groin" or "inguinal junction"). The neck junction is just forward of the junction of the neck and the trunk of the body on both left and right sides. The axillary junction is the junction of the arm and flank around the armpit on both the left and right side. The inguinal junction is the front side of the junction of the leg and the pelvis to the side of the genital on both left and right side. The placement of the device at the neck junction may simulate a severed carotid artery. The placement of the device at the axillary junction may simulate a severed axillary artery. The placement of the device at the inguinal junction may simulate a severed femoral artery.

The multi-junctional bleeding simulator may further include a simulated hemorrhaging wound coupled to the user interface and configured to simulate bleeding, and a blood feed coupled to the simulated hemorrhage wound. The blood feed may be configured to communicate a fluid (e.g., simulated blood) to the simulated hemorrhage wound. In particular, the blood feed may include a simulated blood vessel and associated plumbing. When worn by a wearer (e.g., a live actor), the multi-junctional bleeding simulator may provide for users to safely simulate hemorrhaging in some of the most challenging blood vessels in the most challenging anatomical locations.

The simulated hemorrhaging wound may also be configured to reduce or stop the simulated bleeding (i.e., reduce or substantially stop blood flow) upon proper performance of a hemorrhage control procedure, such as compression and ligation. In this way, the multi-junctional bleeding simulator may further provide the ability for users to safely perform hemorrhage control procedures. For example, the simulated wound of the device may be compressed with emergency trauma dressing to control hemorrhage. The simulated wound cavity or receptacle of the device may be packed with hemostatic gauze or simple gauze to control hemorrhage. Also for example, the simulated blood vessel of the device may be ligated with hemostats or other ligating instruments or material and bandaged with pressure dressings to control hemorrhage.

In an embodiment of the multi-junctional bleeding simulator of the present disclosure, the multi-junctional bleeding simulator may include a top layer of silicone and a bottom layer of silicone adhered around the margins to create a receptacle or cavity, wherein the silicone layers simulate human skin. The top layer of silicone includes an opening simulating a wound to the body such as an abrasion, an excoriation, a hematoma, a laceration, an incision, a puncture wound, a contusion, a crushing injury, or a ballistic trauma.

Penetrating through the bottom layer may be a silicone tube with a first end and a second end. The silicone tube may be elastic, or otherwise non-rigid. The first end of the tube penetrates through the bottom layer of silicone and resides in the receptacle/cavity to simulate a damaged blood vessel. The second end of the tube may be attached to a blood pumping system that supplies blood to the tube to simulate a bleeding damaged blood vessel. The elasticity of the tube allows for the compression and/or ligation to occlude the tube. The receptacle allows the compaction of material into the receptacle to occlude the opening of the tube.

In an alternative embodiment of the multi-junctional bleeding simulator of the present disclosure, the tubing of the multi-junctional bleeding simulator may be replaced with a tubing system. The tubing system includes a primary tube, a feed tube, and an exhaust tube. The primary tube penetrates the bottom layer of silicone and resides in the receptacle. Attached to the primary tube, outside the receptacle, is a Y-connector. The main branch of the Y-connector is attached to the primary tube, the first branch of the Y-connector is connected to the feed tube, and a bypass valve is attached to the second branch of the Y-connector. Attached to the bypass valve is the exhaust tube. The bypass valve is normally closed and fully opens only when a predetermined pressure is met. The bypass valve also has a cracking pressure which opens the bypass valve a small amount. Fluid flow through the exhaust tube will indicate to the user that the proper application of pressure was applied to the wound to slow or stop the bleeding.

As above, it is contemplated that the multi-junctional bleeding simulator of the present disclosure may include the user interface for multiple body locations. In particular, the user interface may be embodied as a multi-junctional attachment unit that facilitates the attachment of the multi-junctional bleeding simulator to various locations on a live actor. The multi-junctional attachment unit may include an adjustable limb strap, a neck strap, and/or an extended strap. The multi-junctional attachment unit with the adjustable limb strap facilitates attachment to the axillary and inguinal junctions, the neck strap facilitates attachment to the neck junction, and the extended strap facilitates the attachment to the axillary junction and the inguinal junction of a live actor. The Multi-Junctional Attachment Device includes a base protection layer, a padding layer, and a cover. The base layer is a puncture and cut resistant layer to protect the live actor wearing the multi-junctional bleeding simulator. The padding layer increases stability and decreases the movement of the multi-junctional bleeding simulator when worn. The cover provides a uniform look and color to the multi-junctional attachment unit.

Referring initially to FIG. 1, a perspective view of a multi-junctional bleeding simulator in accordance with one exemplary embodiment of the present disclosure is shown and generally designated 100. The multi-junctional bleeding simulator 100, when used by a live actor, allows users to safely simulate hemorrhaging in some of the most challenging blood vessels such as the carotid artery, the axillary artery, and the femoral artery located in the most challenging anatomical locations. The multi-junctional bleeding simulator 100 provides real-time hemorrhage that can be controlled in real-time by performing the correct hemorrhage control procedures, such as compression and ligation. The multi-junctional bleeding simulator 100 may be compressed with direct pressure from a person or emergency trauma dressing, may be packed with hemostatic or simple gauze, ligated with hemostats or other ligating instruments or material, and bandaged with pressure dressings to control the simulated hemorrhage. The application of the multi-junctional bleeding simulator 100 on a live actor allows the live actor to provide the responses and actions of an injured person to provide an additional level of realism that a medical mannequin cannot provide.

Figure 2:
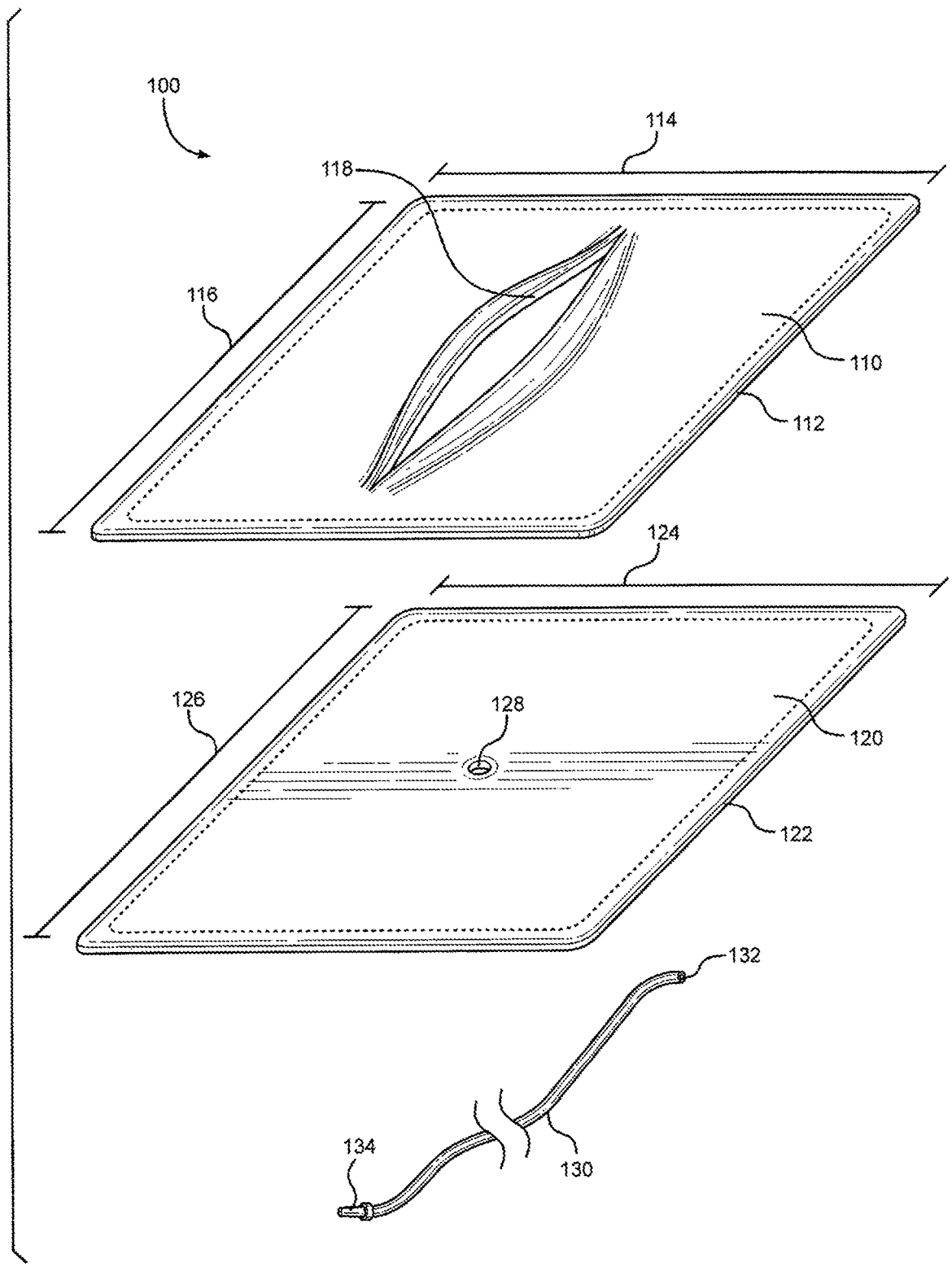
FIG. 2 is an exploded view of the multi-junctional bleeding simulator, showing a first silicone layer simulating skin with an open wound, a second silicone layer simulating skin, and a silicone tube simulating a blood vessel, according to one embodiment of the disclosure.

Referring now to FIG. 2, an exploded view of the multi-junctional bleeding simulator 100 is shown. As shown, the multi-junctional bleeding simulator 100 may include an outer layer (e.g., a top silicone layer 110), an inner layer (e.g., a second or bottom silicone layer 120), and a simulated blood vessel (e.g., a silicone tube 130). The outer layer and the inner layer may be peripherally joined together or otherwise formed to create a simulated wound receptacle or cavity, and the simulated blood vessel may be inserted into the simulated wound receptacle such that simulated blood may be introduced into the cavity via the simulated blood vessel and egress the cavity via the simulated wound.

The top silicone layer 110 may be constructed of silicone and simulated to look and feel like human skin. This may include manufacturing the top silicone layer 110 with surface texture to mimic certain portions of the human skin and adding color. As shown, the top silicone layer 110 may have a length 114, a width 116, and a peripheral margin 112. Also as shown, an opening 118 constructed to simulate a wound may be located approximately in the center of the top silicone layer 110. The wound can be of any variety such as an abrasion, an excoriation, a hematoma, a laceration, an incision, a puncture wound, a contusion, a crushing injury, or a ballistic trauma. In the multi-junctional bleeding simulator 100, the opening 118 may be constructed to simulate a laceration.

The bottom silicone layer 120 may be constructed of silicone and simulated to look and feel like human skin similar to top silicone layer 110. As above, the bottom silicone layer 120 may have a length 124, width 126, and a peripheral margin 122. According to one embodiment, the bottom silicone layer 120 may include a hole 128 to accommodate the silicone tube 130, which may be located off-center in the bottom silicone layer 120, or otherwise in "misalignment" with the opening 118 of the top silicone layer 110.

The silicone tube 130, having a first end 132 and a second end 134, is inserted through the hole 128 where a small section of the silicone tube 130 adjacent the first end 132 is placed. The location of the opening 118 and the hole 128 is not meant to be limiting and it is contemplated that the location of the opening 118 and the hole 128 may be changed to simulate a particular wound.

As shown, the top silicone layer 110 and the bottom silicone layer 120 may have substantially the same dimensions. Further, the top silicone layer 110 and the bottom silicone layer 120 may be aligned and attached together at their respective peripheral margins 112 and 122 creating the simulated wound receptacle/cavity (receptacle 140, shown in FIG. 1) with a volume defined by the surface area of the top silicone layer 110 within the peripheral margin 112 and the surface area of the bottom silicone layer 120 within peripheral margin 122. The ability of silicone to stretch provides a dynamic volume for the receptacle 140 where the maximum volume is at the silicone's maximum stretched dimensions. When not stretched, the volume of the receptacle 140 is approximately zero as the top silicone layer 110 lies flat against the bottom silicone layer 120. When stretched, the volume of the receptacle 140 changes to accommodate the needed volume. The receptacle 140 is accessible through the opening 118. The opening 118 also provides access to the section of silicone tube 130 adjacent the first end 132 residing in the receptacle 140.

It is contemplated that the bottom silicone layer 120 may have larger dimensions than the top silicone layer 110, where the peripheral margin 122 of the bottom silicone layer 120 will not align with the peripheral margin 112 of the top silicone layer 110. In this instance the top silicone layer 110 will be attached to the bottom silicone layer 120 where the respective peripheral margins will not align. The volume will be defined by the surface area of the top silicone layer 110 within the peripheral margin 112 and the bottom silicone layer 120 within peripheral margin 112 of the silicone layer. The shape of the top silicone layer 110 and the bottom silicone layer 120 is not meant to be limiting and it is contemplated that the top silicone layer 110 and the bottom silicone layer 120 may be circular, semi-circular, rectangular, quadrilateral, or any other shape needed to simulate a particular wound.

Figure 3:
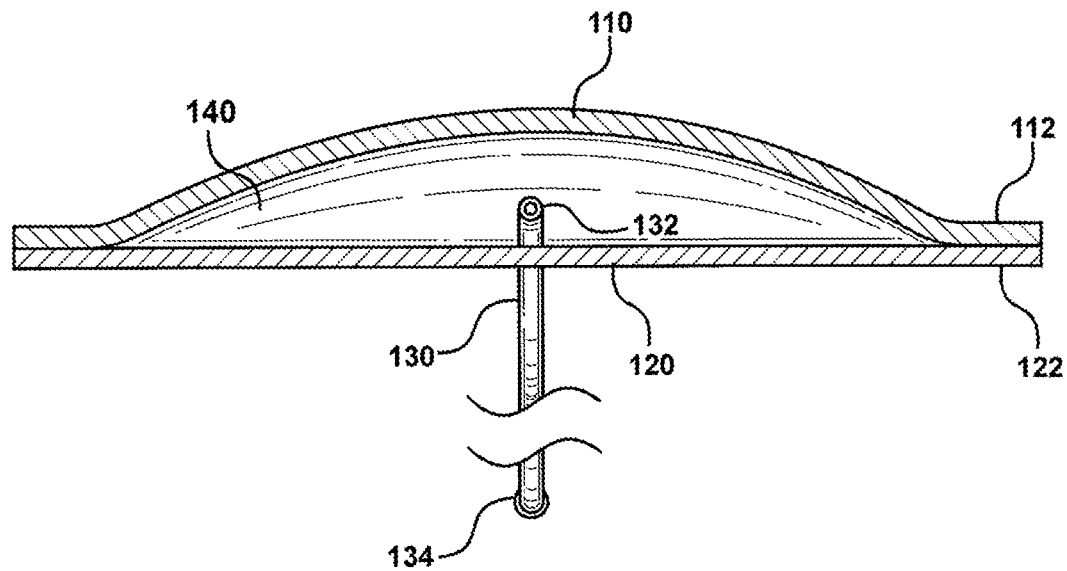
FIG. 3 is a cutaway view of the multi-junctional bleeding simulator, taken along lines 3-3 of FIG. 1, according to one embodiment of the disclosure.

Referring now to FIG. 3, a cutaway view of the multi-junctional bleeding simulator 100 taken along lines 3-3 of FIG. 1 is shown. As shown, the multi-junctional bleeding simulator 100 includes the top silicone layer 110 attached to the bottom silicone layer 120 at the peripheral margins 112 and 122, respectively. The top silicone layers 110 and the bottom silicone layer 120 have been stretched to increase the volume of receptacle 140 of the multi-junctional bleeding simulator 100 to show the first end 132 of silicone tube 130 within the receptacle 140.

Figure 4:
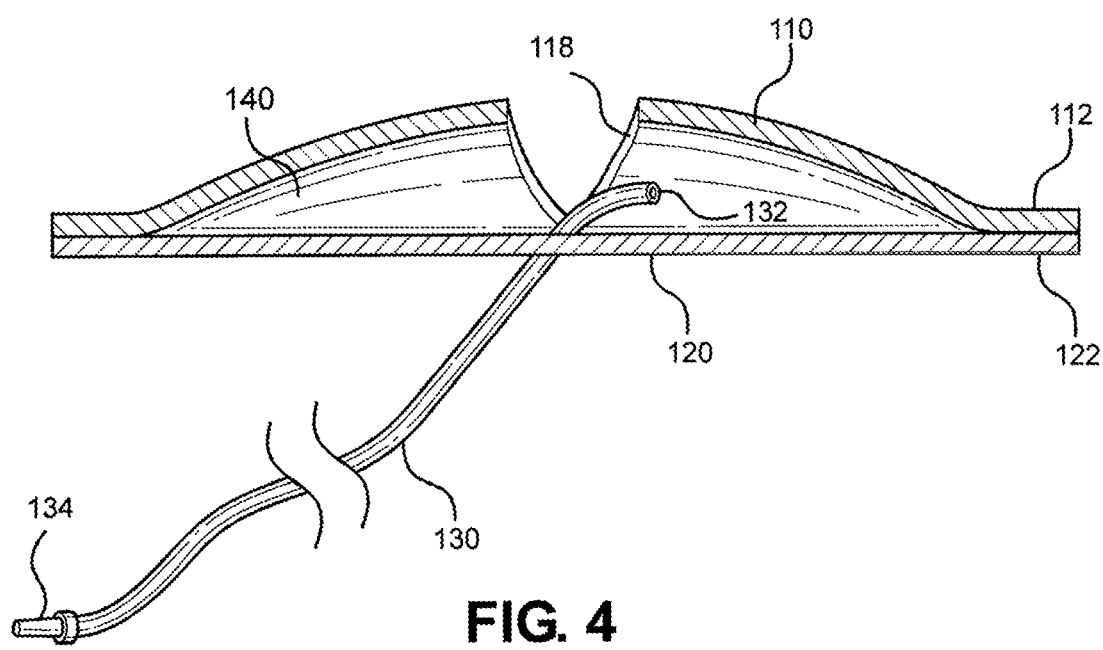
FIG. 4 is a cutaway view of the multi-junctional bleeding simulator, taken along lines 4-4 of FIG. 1, according to one embodiment of the disclosure.

Referring now to FIG. 4, a cutaway view of the multi-junctional bleeding simulator 100 taken along lines 4-4 of FIG. 1 is shown. As shown, the multi-junctional bleeding simulator 100 includes the top silicone layer 110 attached to the bottom silicone layer 120 at the peripheral margins 112 and 122, respectively. The top silicone layers 110 and the bottom silicone layer 120 have been stretched to increase the volume of receptacle 140 of the multi-junctional bleeding simulator 100 to show the first end 132 of silicone tube 130 within the receptacle 140. Opening 118 provides access to the receptacle 140 and the first end 132 of silicone tube 130.

Figure 5:
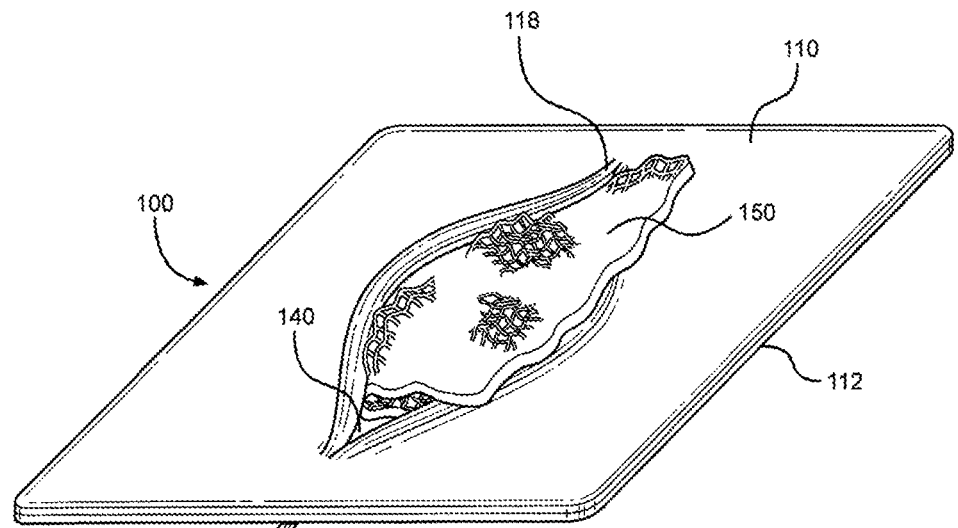
FIG. 5 is a perspective view of the multi-junctional bleeding simulator, showing the simulated wound compacted with gauze to stop the simulated wound from bleeding, according to one embodiment of the disclosure.

Referring now to FIG. 5, the multi-junctional bleeding simulator 100 is shown simulating a hemorrhaging wound. The top silicone layer 110 simulates the skin of a human where the opening 118 simulates an open wound and the receptacle 140 simulates an open cavity. In the multi-junctional bleeding simulator 100, the silicone tubing may have diameter of approximately 0.5 inches. The first end 132 (not shown) of the silicone tube 130 simulates a ruptured blood vessel within the open the open cavity. The second end 134 of silicone tubing 130 is attached to a blood pumping system capable of flowing simulated blood up to 0.75 liters per minute. The blood pumping system provides a fluid flow of simulated blood in direction 152 into the silicone tubing 130. This provides simulated bleeding through the first end 132 to simulate a hemorrhaging wound where a user may practice the application of gauze 150 to stop a bleeding wound. In particular, the multi-junctional bleeding simulator 100 may simulate an injury to the carotid artery at the neck junction, the axillary artery at the axillary junction, and the femoral artery at the inguinal junction.

As shown, the receptacle 140 has been packed with gauze 150 through opening 118 to attempt to stop the bleeding. The use of hemostatic gauze 150 to stop bleeding from hemorrhaging wounds is known in the art and has been implemented in the field for many years. Generally, to stop the bleeding from a traumatic injury using a packing material such as gauze 150, it is recommended that pressure be first applied to the general vicinity of the wound to control the bleeding, as the gauze 150 and other supplies are retrieved for use. Once the gauze 150 and supplies are retrieved, the specific location of the bleed should be identified and direct pressure applied. The wound should then be packed with the gauze 150 until no more gauze 150 may be inserted and then wrapped with pressure dressings to provide pressure on the gauze and wound.

According to one embodiment, the multi-junctional bleeding simulator 100 may simulate a bleeding wound and may be packed with gauze 150 to stop bleeding, in order to train users and prepare them for real world situations. To stop the multi-junctional bleeding simulator 100 from bleeding using a packing material such as gauze 150, pressure may be first applied to multi-junctional bleeding simulator 100 over the general vicinity of the opening 118 to control the bleeding as the gauze 150 and other supplies are retrieved. By applying pressure over the general vicinity of the opening 118, the first end 132 of the silicone tube 130 may be compressed making the opening 118 narrow and slowing blood flow out of the silicone tube 130.

Once the gauze 150 and supplies are retrieved, the opening 118 may be stretched to access the receptacle 140 to identify the specific location of the bleed, the first end 132 of the silicone tube 130. Direct pressure can then be applied to the first end 132 of the silicone tube 130 to stop bleeding and the receptacle 140 may be packed with gauze 150 until no more gauze 150 can be packed, which should stop the bleeding.

To stop the multi-junctional bleeding simulator 100 from pumping blood into the silicone tube 130, the blood pumping system can be turned off once the procedure is complete or the blood pumping system may be fitted with a pressure sensor that turns off the pumping mechanism when a predetermined pressure in the silicone tube 130 is reached.

Figure 6:
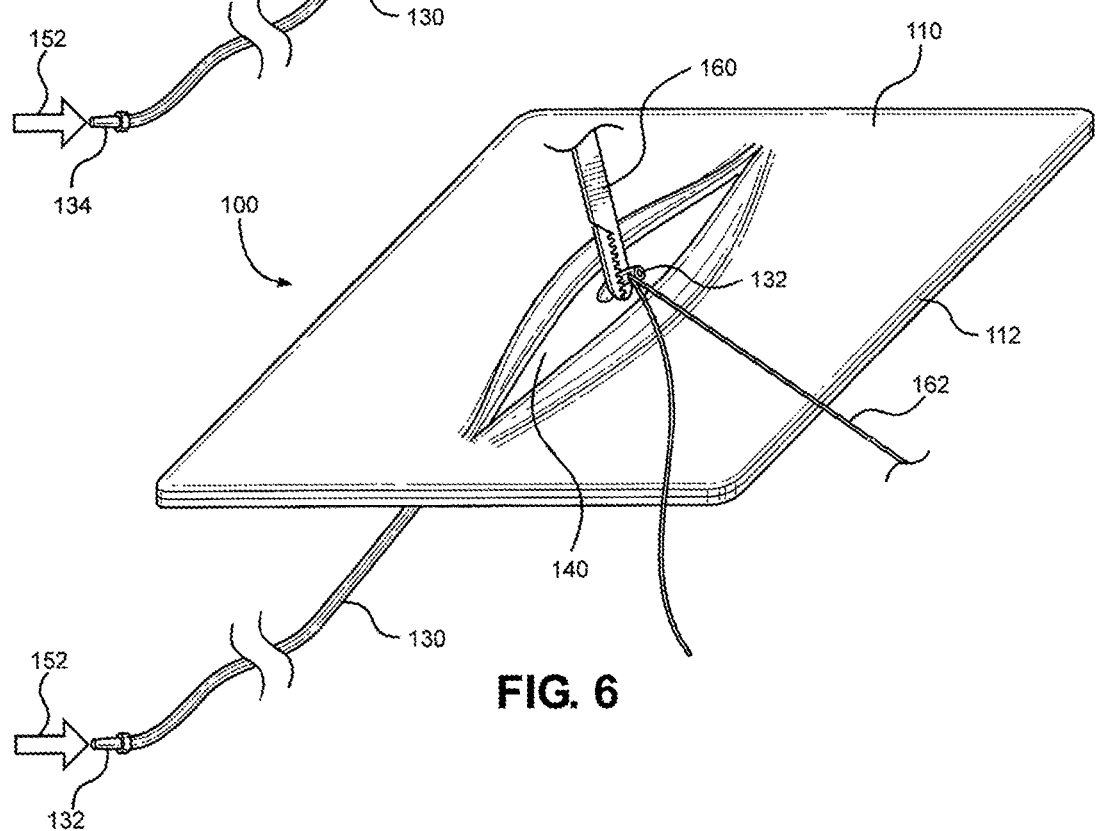
FIG. 6 is a perspective view of the multi-junctional bleeding simulator, showing the simulated blood vessel being ligated to stop the simulated wound from bleeding, according to one embodiment of the disclosure.

Referring now to FIG. 6, the multi-junctional bleeding simulator 100 is shown simulating a hemorrhaging wound. The top silicone layer 110 simulates the skin of a human where the opening 118 simulates an open wound and the receptacle 140 simulates an open cavity. The first end 132 of the silicone tube 130 simulates a ruptured blood vessel within the open the open cavity. The second end 134 of silicone tubing 130 is attached to a blood pumping system. The blood pumping system provides a fluid flow of simulated blood in direction 152 into the silicone tubing 130. This provides simulated bleeding through the first end 132 to simulate a hemorrhaging wound where a user may practice the ligation to stop a bleeding wound.

As shown, the first end 132 of the silicone tube 130 has been clamped with a clamp 160 and tied with a suture 162. Ligation to stop bleeding from hemorrhaging wounds is known in the art and has been implemented in the field for many years, but is not as quick, easy, or simple as packing a bleeding wound with gauze to stop the bleeding. Ligation requires more training compared to packing wounds with gauze. Generally, to stop the bleeding from a traumatic injury by ligation, it is recommended that pressure be first applied to the general vicinity of the wound to control the bleeding as a clamp 160, sutures 162, and other supplies are retrieved for use. Once the clamp 160, sutures 162, and other supplies are retrieved, the wound should be explored to identify the ruptured blood vessel. Once identified, the ruptured blood vessel/s should be clamped with clamp 160 and ligated with sutures 162 to stop the bleeding.

The multi-junctional bleeding simulator 100 simulates a bleeding wound and may be ligated to stop bleeding in order to train users and prepare them for real world situations. To stop the multi-junctional bleeding simulator 100 from bleeding by ligating the simulated blood vessel, pressure may be first applied to multi-junctional bleeding simulator 100 over the general vicinity of the opening 118 to control the bleeding as the clamp 160, sutures 162, and other supplies are retrieved for use. By applying pressure over the general vicinity of the opening 118, the first end 132 of the silicone tube 130 may be compressed making the opening narrow and slowing down the bleed. Once clamp 160, sutures 162, and supplies are retrieved, the opening 118 may be stretched to access the receptacle 140 to identify the specific location of the bleed, the first end 132 of tube 130. The clamp 160 can then be applied to the first end 132 of the silicone tube 130 to stop bleeding. Once clamped, the first end 132 of the silicone tube 130 may be ligated with sutures 162. To stop the multi-junctional bleeding simulator 100 from pumping blood into the silicone tube 130, the blood pumping system can be turned off once the procedure is complete or the blood pumping system may be fitted with a pressure sensor that turns off the pumping mechanism when a predetermined pressure in the silicone tube 130 is reached.

Figure 7:
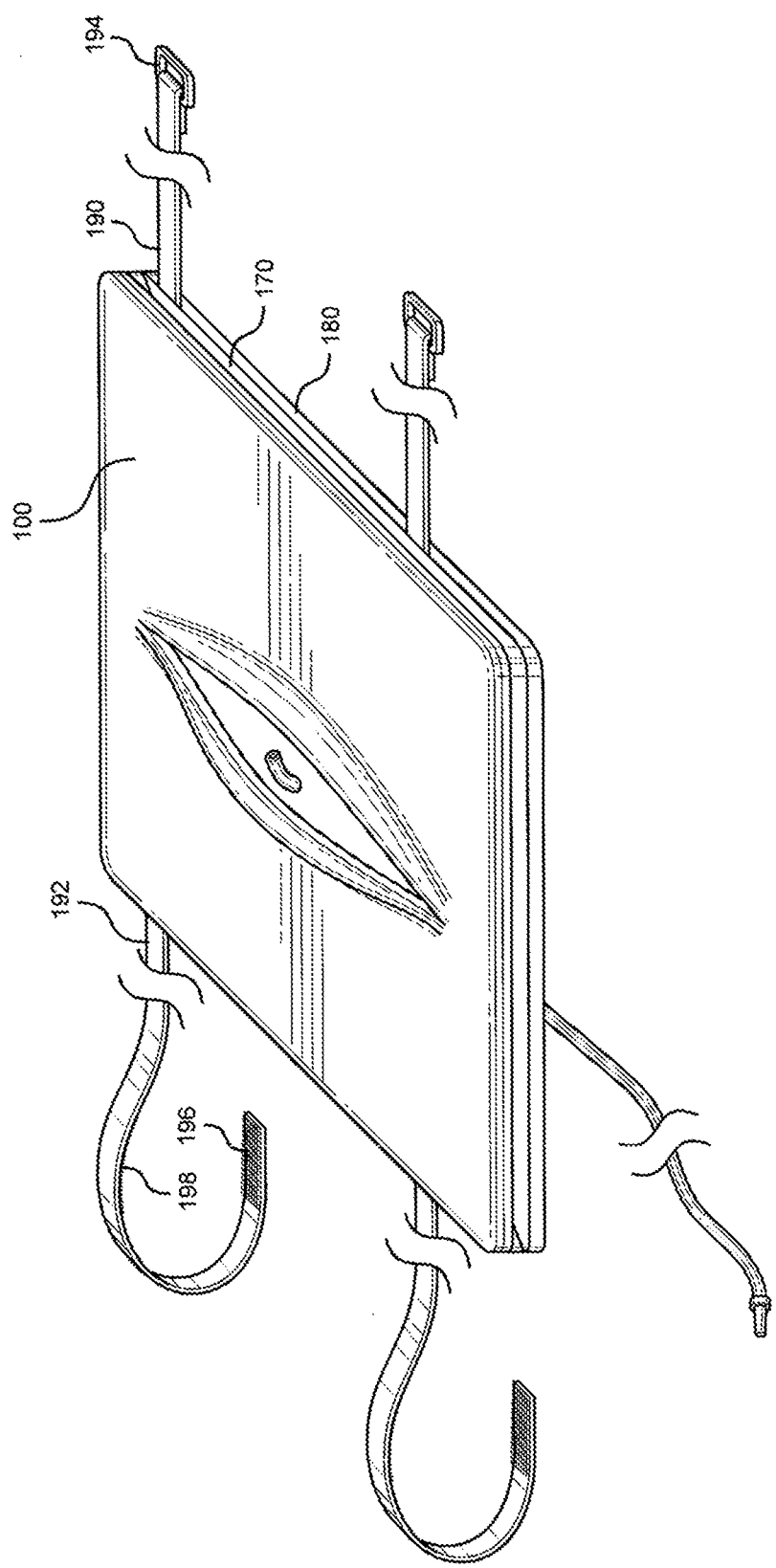
FIG. 7 is a perspective view of the multi-junctional bleeding simulator, configured as a wearable medical training device (e.g., including a protective layer, a padding layer, and securing straps), according to one embodiment of the disclosure.
Figure 8:
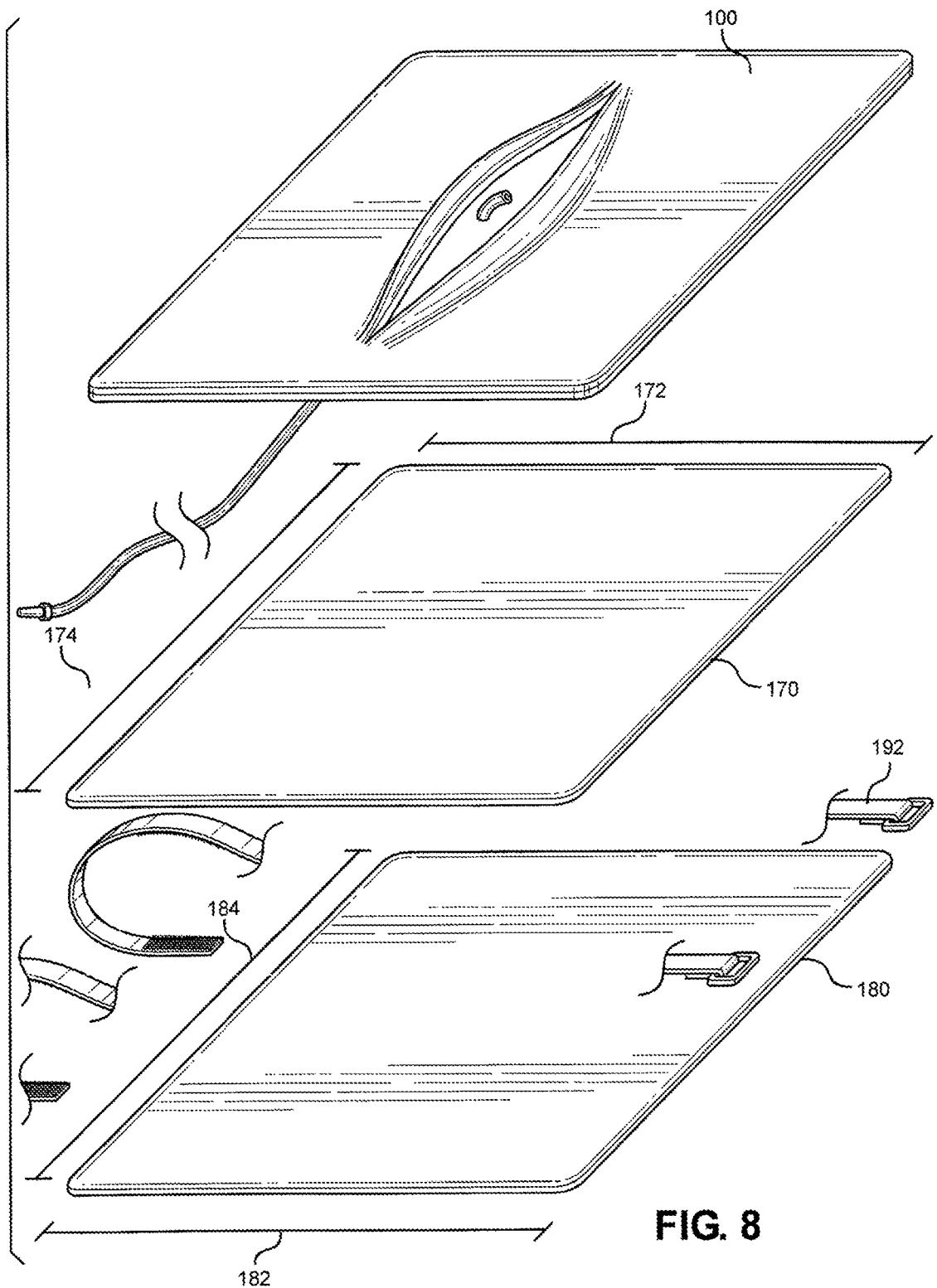
FIG. 8 is an exploded view of the multi-junctional bleeding simulator, with a protective layer, a padding layer, and securing straps, according to one embodiment of the disclosure.

Referring now to FIG. 7, the multi-junctional bleeding simulator 100, described in conjunction with FIG. 8, is shown with a user interface, generally including a protective layer 170, a layer of padding 180, and securing straps 190. The protective layer 170 may have a length 172 and width 174, and may be attached to the underside of the multi-junctional bleeding simulator 100.

The protective layer 170 may be made of a layer of ABS with a neoprene coating that is puncture and cut resistant. The protective layer 170 provides a safety barrier to prevent the live actor from being harmed during rigorous training activities. The padding layer 180 may also have a length 182 and width 184, and may be attached to the underside of the protective layer 170. The padding layer 180 may be configured to contact and conform itself around the live actor, and further to provide a friction surface to decrease the movement of the multi-junctional bleeding simulator 100 when used in dynamic training.

The securing straps 190 may include two straps attached to the underside of the protective layer 170, placed between the protective layer 170 and the padding layer 180. Each securing strap 190 may include a strap 192 with a fastener (e.g., here, a square buckle 194) at one end, and a receiver (e.g., here, a hook portion 196) at the opposite end, with a loop portion 198 adjacent the hook portion 196. This allows for the adjustment of the length of the strap 192 when used to secure the multi-junctional bleeding simulator 100 to a live actor. It is contemplated that the strap 192 may be fitted with different types of clasps, buckles, and fasteners.

Figure 9:
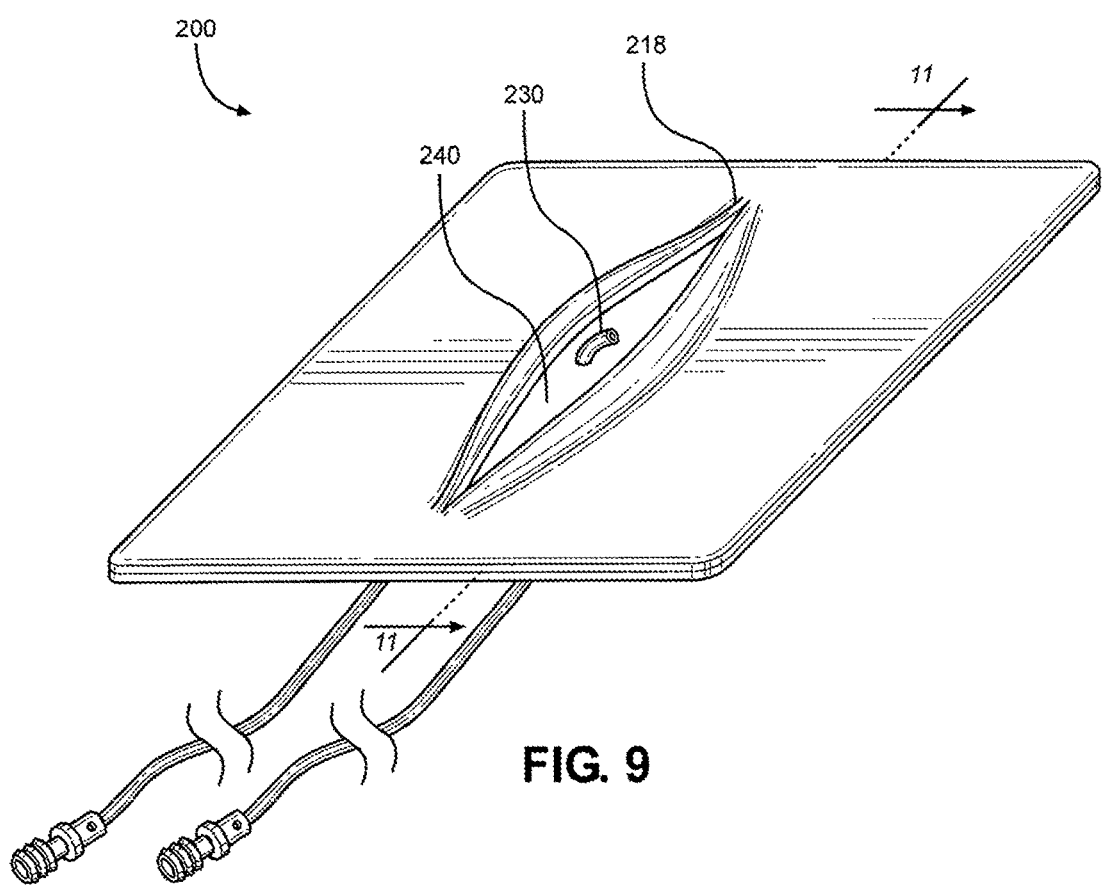
FIG. 9 is a perspective view of the multi-junctional bleeding simulator, showing a simulated wound with a simulated blood vessel, according to an alternate embodiment of the disclosure.
Figure 10:
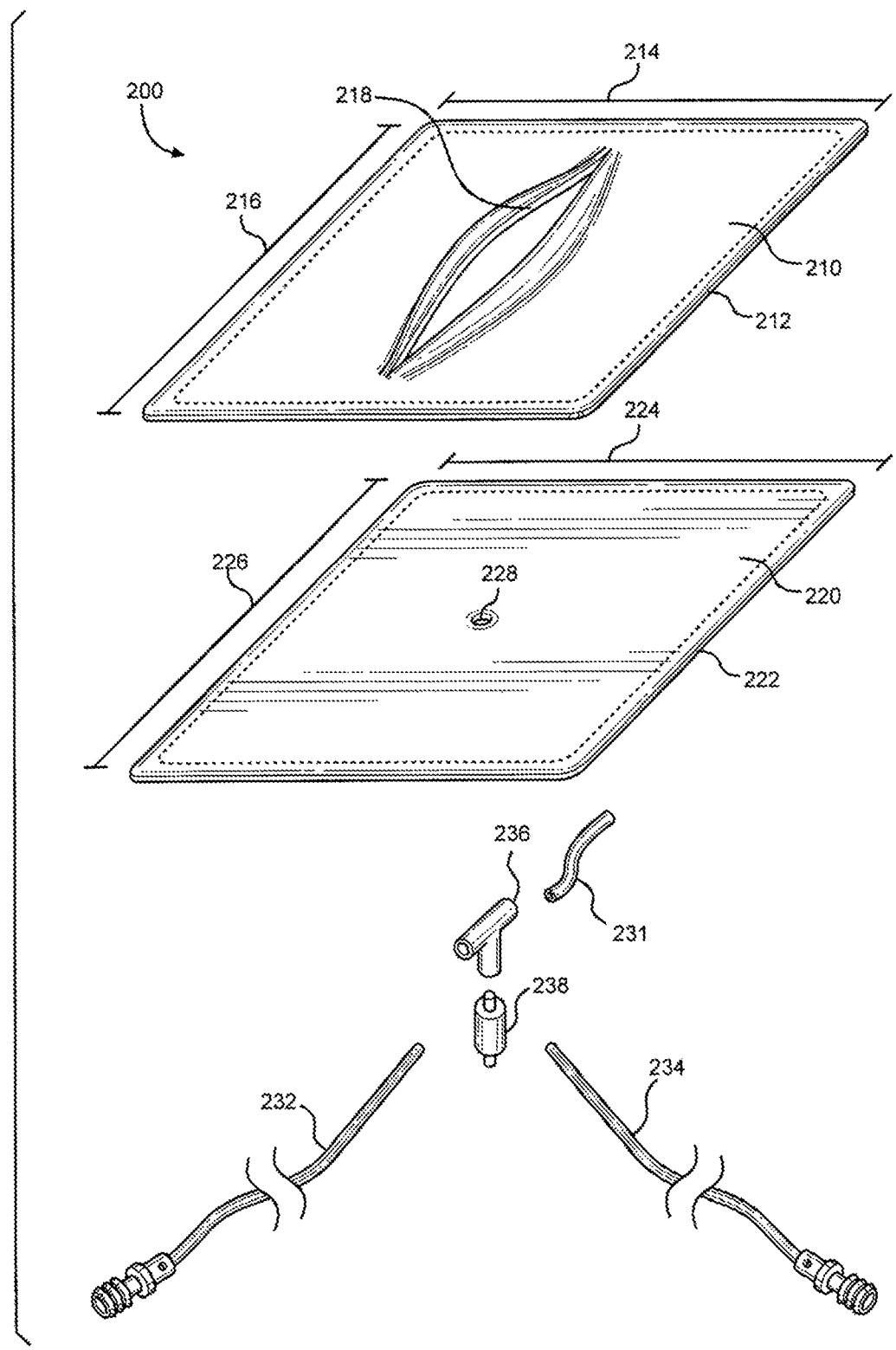
FIG. 10 is an exploded view of multi-junctional bleeding simulator, showing a first silicone layer simulating skin with an open wound, a second silicone layer simulating skin, and a tubing system simulating a blood vessel system, according to one embodiment of the disclosure.

Referring now to FIG. 9, a perspective view of an alternative embodiment of the multi-junctional bleeding simulator in accordance with the present disclosure is shown and generally designated 200. The multi-junctional bleeding simulator 200, described in conjunction with FIG. 10, includes a top silicone layer 210, a second silicone layer 220, and a tubing system 230.

The top silicone layer 210 is constructed of silicone and simulated to look and feel like human skin. This includes manufacturing the top silicone layer 210 with surface texture to mimic certain portions of the human skin and adding color. The top silicone layer 210 has a length 214, width 216, and a peripheral margin 212. Located approximately in the center of the top silicone layer 210 is an opening 218 constructed to simulate a wound. The wound can be of any variety such as an abrasion, an excoriation, a hematoma, a laceration, an incision, a puncture wound, a contusion, a crushing injury, or a ballistic trauma. In the preferred embodiment, the opening 218 is constructed to simulate a laceration.

The bottom silicone layer 220 is constructed of silicone and simulated to look and feel like human skin, similar to top silicone layer 210. The bottom silicone layer 220 has a length 224, width 226 and a peripheral margin 222. Located off center in the bottom silicone layer 220 is a hole 228 to accommodate the tubing system 230.

The top silicone layer 210 and the bottom silicone layer 220 may be substantially similar to the top silicone layer 110 and the bottom silicone layer 110 of the multi-junctional bleeding simulator 100 and may be attached in substantially the same way. Here, the top silicone layer 210 and the bottom silicone layer 220 have the same dimensions. The top silicone layer 210 and the bottom silicone layer 220 are aligned and attached together at their respective peripheral margins 212 and 222 creating a simulated wound receptacle/cavity (receptacle 240) with a volume generally defined by the surface of the top silicone layer 210 within the peripheral margin 212 and the bottom silicone layer 220 within peripheral margin 222. As above, the ability of silicone to stretch provides a dynamic volume for the receptacle 240. When not stretched, the volume of the receptacle 240 is approximately zero as the top silicone layer 210 lies flat against the bottom silicone layer 220. When stretched, the volume of the receptacle 240 changes. The receptacle 240 is accessible through the opening 218. The opening 218 also provides access to the section of tubing system 230 residing in the receptacle 240.

As illustrated, the tubing system 230 may generally include a primary tube 231, a feed tube 232 and an exhaust tube 234. The primary tube 231 enters the receptacle 240, for example, penetrating through the hole 228 of the bottom silicone layer 220, and may partially reside in the receptacle 240.

As shown a Y-connector 236 may be attached to the primary tube 231, outside the receptacle 240. The main branch of the Y-connector 236 is attached to the primary tube 231, the first branch of the Y-connector 236 is connected to the feed tube 232, and the second branch of the Y-connector 236 is attached to a bypass valve 238. Attached to the bypass valve 238 is the exhaust tube 234.

According to one embodiment, the bypass valve 238 may be normally closed, and may fully open only when a predetermined pressure is met. The bypass valve 238 may also have a cracking pressure which partially opens the bypass valve 238 when pressure is present in the system.

The feed tube 232 is provided with a fluid flow by a blood pumping system. The feed tube 232 provides a fluid flow pathway from the blood pumping system to the first branch of the Y-connecter 236. The bypass valve 238 is normally closed and prevents fluid flow through the second branch of the Y-connecter 236. As a result, the fluid flows through the main branch of the Y-connector 236 and out the primary tube 234 under normal conditions. Under circumstances where the primary tube 234 is restricted, the back pressure in the primary tube 231 may open the bypass valve 238. Depending on the pressure in the primary tube 231, the bypass valve 238 may be either partially open or fully open. In either circumstance, fluid will begin to flow into the exhaust tube 234. Attached to the exhaust tube 234 may be a reservoir (not shown). The reservoir may be transparent or semi-transparent to show that fluid has flowed into the reservoir indicating that the fluid flow through primary tube 231 was restricted.

Figure 11:
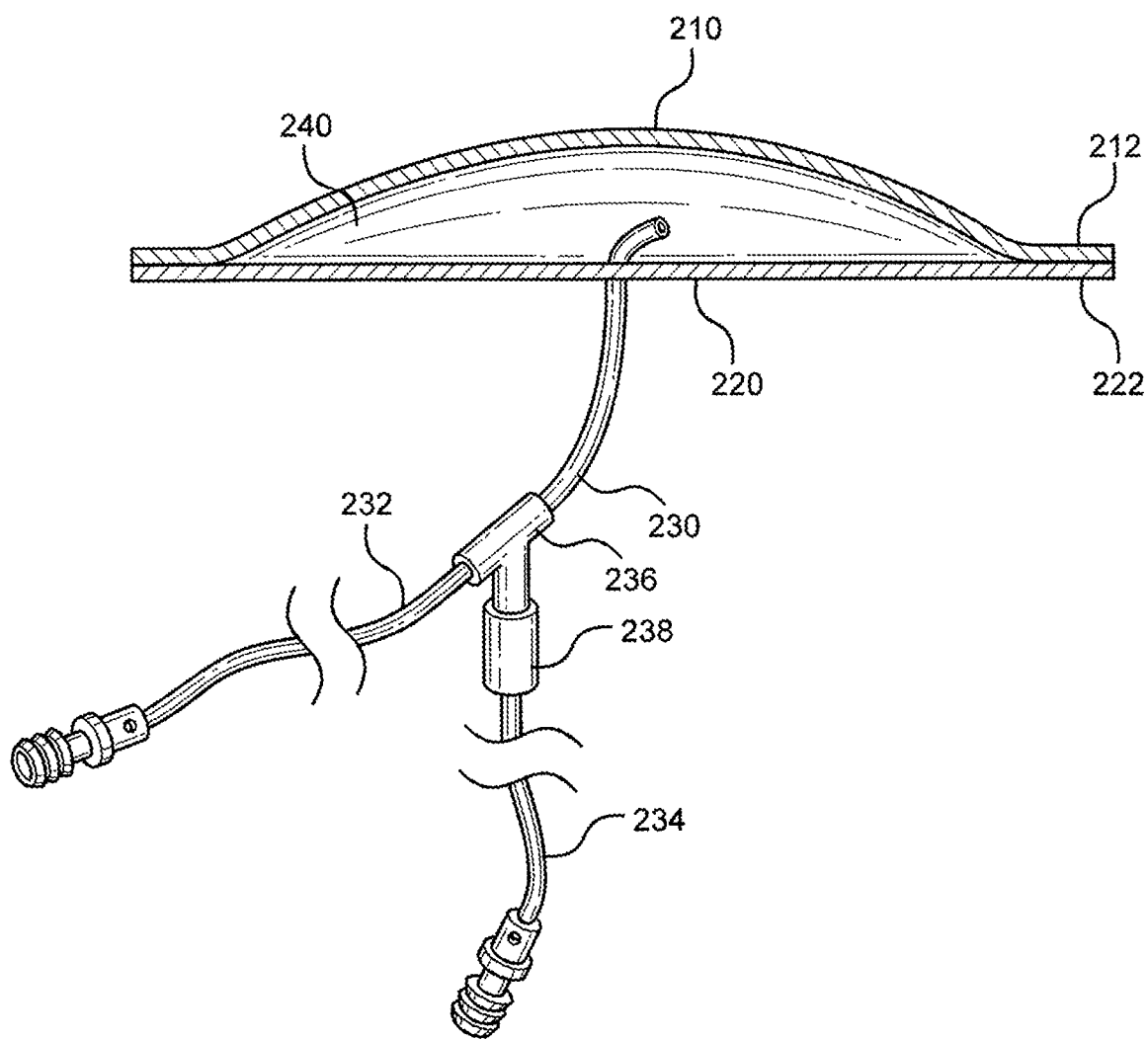
FIG. 11 is a cutaway view of the multi-junctional bleeding simulator, taken along lines 11-11 of FIG. 9, according to one embodiment of the disclosure.

Referring now to FIG. 11, a cutaway view of the multi-junctional bleeding simulator 200 taken along lines 11-11 of FIG. 9 is shown. As shown, the multi-junctional bleeding simulator 200 includes the top silicone layer 210 attached to the bottom silicone layer 220 at the peripheral margins 212 and 222, respectively. The top silicone layers 210 and the bottom silicone layer 220 have been stretched to increase the volume of receptacle 240 of the multi-junctional bleeding simulator 200 to show the primary tube 231 of the tubing system 230 within the receptacle 240.

Figure 12:
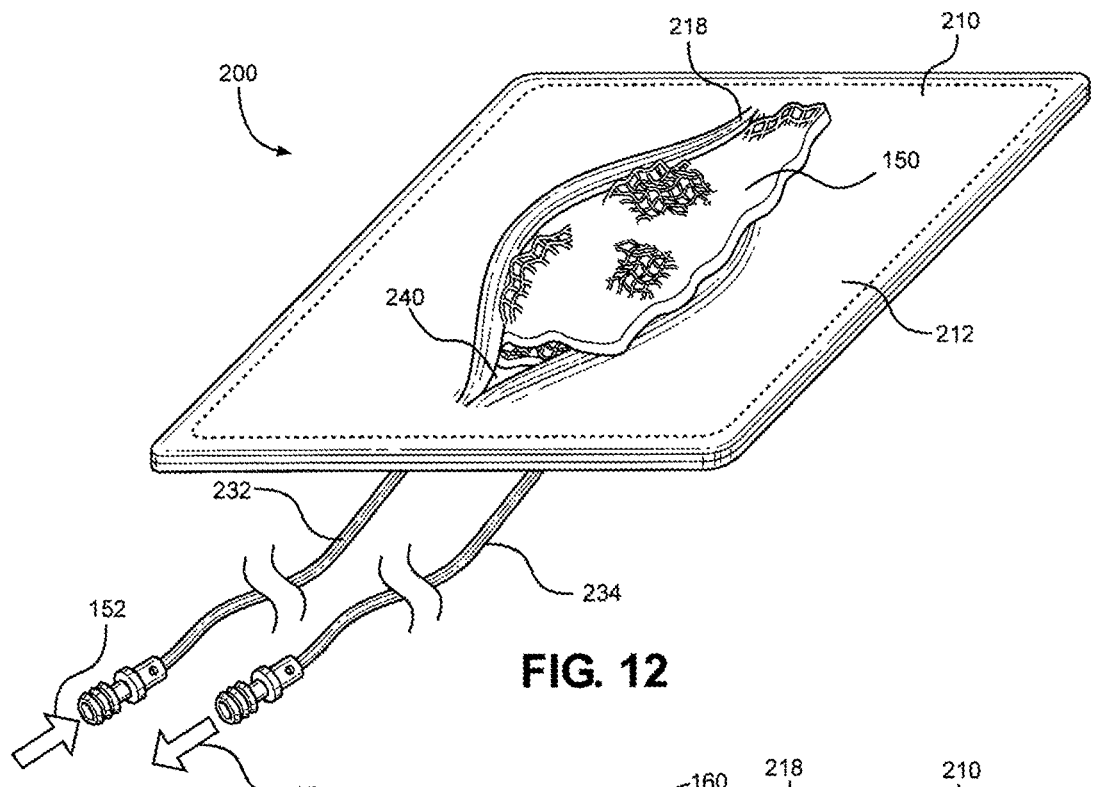
FIG. 12 is a perspective view of the alternative embodiment of the multi-junctional bleeding simulator, showing the simulated wound compacted with gauze to stop the simulated wound from bleeding, according to one embodiment of the disclosure.

Referring now to FIG. 12, the multi-junctional bleeding simulator 200 is shown simulating a hemorrhaging wound. The top silicone layer 210 simulates the skin of a human where the opening 218 simulates an open wound and the receptacle 240 simulates an open cavity. The primary tube 231 (not shown) simulates a ruptured blood vessel within the open cavity 240. The feed tube 232 is attached to a blood pumping system. The blood pumping system provides a fluid flow of simulated blood in direction 152 into the feed tube 232. This provides simulated bleeding through the primary tube 231 of the tubing system 230 to simulate a hemorrhaging wound where a user may practice the application of gauze 150 to stop a bleeding wound where gauze is used to stop bleeding.

As shown, the receptacle 240 has been packed with gauze 150 through opening 218 to attempt to stop the bleeding. The multi-junctional bleeding simulator 200 simulates a bleeding wound and may be packed with gauze 150 to stop bleeding in order to train users and prepare them for real world situations. To stop the multi-junctional bleeding simulator 200 from bleeding using a packing material such as gauze 150, pressure may be first applied to multi-junctional bleeding simulator 200 over the general vicinity of the opening 218 to control the bleeding. as the gauze 150 and other supplies are retrieved for use.

By applying pressure over the general vicinity of the opening 218, the primary tube 231 of the tubing system 230 may be compressed making the opening narrow. This will create backpressure in the tubing system 230 and will either partially open or fully open the bypass valve 238 to flow fluid through the exhaust tube 234 in direction 154 and into a transparent or semi-transparent reservoir. Fluid flow through the exhaust tube 234 and within the reservoir will indicate to the user that the proper application of pressure was applied to the wound to slow or stop the bleeding.

Once the gauze 150 and supplies are retrieved for use, the opening 218 may be stretched open to access the receptacle 240, and to identify the specific location of the bleed (the primary tube 231 of the tubing system 230). When taking the pressure off the general vicinity of the wound, the bypass valve 238 closes and the maximum fluid flow of the fluid flows through the primary tube 231.

Once the primary tube 231 is found, due to the flowing fluid, direct pressure can then be applied to the primary tube 231 to stop the bleeding, and the receptacle 240 may be packed with gauze 150 until no more gauze 150 can be packed, which should stop the bleeding.

If the gauze 150 was properly packed into the wound, the primary tube 231 should be occluded, and the bypass valve 238 should be fully open due to the back pressure created by the occluded primary tube 231 meeting the opening pressure of the bypass valve 238. The maximum fluid flow of the fluid then flows through the exhaust tube 234 and fills the reservoir, indicating that the wound was properly packed and occluded.

If the gauze 150 was not properly packed, the primary tube 231 will still flow fluid indicating that the primary tube 231 was not properly occluded. This will create a marginal amount of back pressure in the tubing system 230. This back pressure will partially open the bypass valve 238 and a slow trickle of fluid flows through the exhaust tube 234 and fills the reservoir, providing an additional indicator that the wound was not properly packed and occluded.

Figure 13:
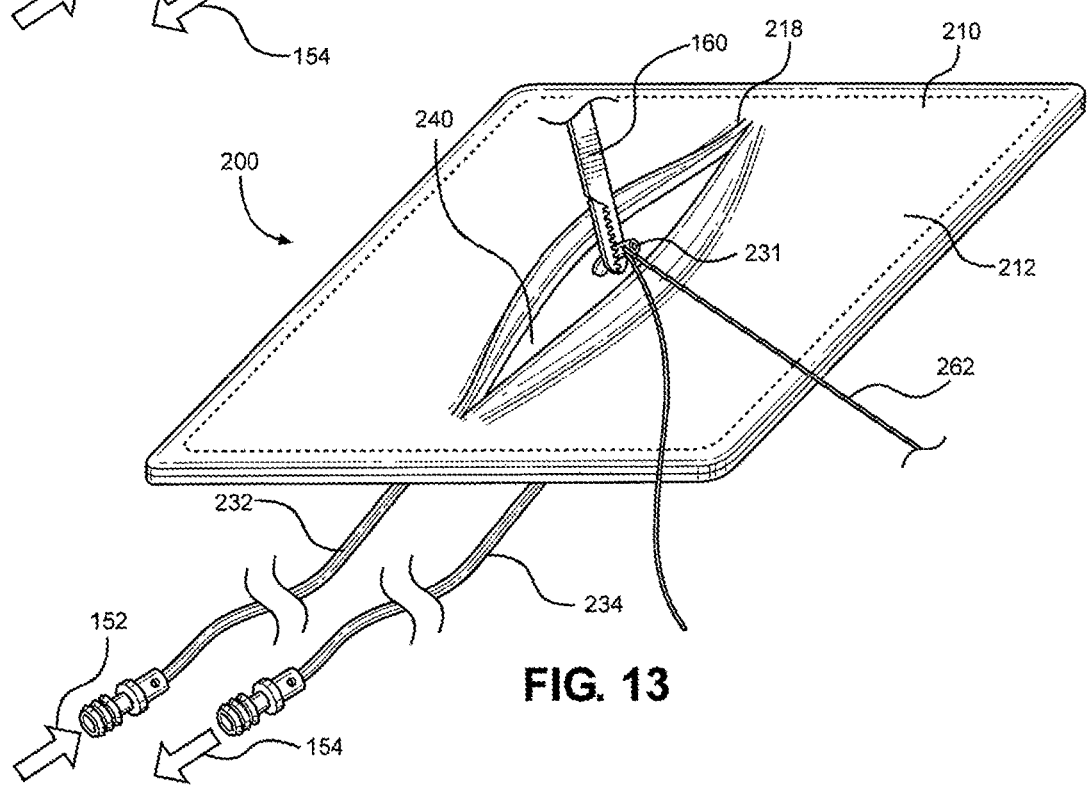
FIG. 13 is a perspective view of the alternative embodiment of the multi-junctional bleeding simulator, showing the simulated blood vessel being ligated to stop the simulated wound from bleeding, according to one embodiment of the disclosure.

Referring now to FIG. 13, the multi-junctional bleeding simulator 200 is shown simulating a hemorrhaging wound where ligation is used to stop bleeding. The top silicone layer 210 simulates the skin of a human where the opening 218 simulates an open wound and the receptacle 240 simulates an open cavity. The primary tube 231 simulates a ruptured blood vessel within the open cavity 240. The feed tube 232 is attached to a blood pumping system. The blood pumping system provides a fluid flow of simulated blood in direction 152 into the feed tube 232. This provides simulated bleeding through the primary tube 231 of the tubing system 230 to simulate a hemorrhaging wound where a user may practice ligation to stop a bleeding wound.

As shown, the primary tube 231 has been clamped with a clamp 160 and tied with a suture 262. The multi-junctional bleeding simulator 200 simulates a bleeding wound and may be ligated to stop bleeding in order to train users and prepare them for real world situations. As above, to stop the multi-junctional bleeding simulator 200 from bleeding by ligating the simulated blood vessel, pressure may be first applied to multi-junctional bleeding simulator 200 over the general vicinity of the opening 218 to control the bleeding, as the clamp 160, sutures 262, and other supplies are retrieved for use.

By applying pressure over the general vicinity of the opening 218, the primary tube 231 of the tubing system 230 may be compressed making the opening narrow. This will create backpressure in the tubing system 230 and will either partially open or fully open the bypass valve 238 to flow fluid through the exhaust tube 234 in direction 154 and into a transparent or semi-transparent reservoir. Fluid flow through the exhaust tube 234 and within the reservoir will indicate to the user that the proper application of pressure was applied to the wound to slow or stop the bleeding.

Once clamp 160, sutures 262, and supplies are retrieved for use, the opening 218 may be stretched open to access the receptacle 240, and to identify the specific location of the bleed, (the primary tube 231 of the tubing system 230). When taking the pressure off the general vicinity of the wound, the bypass valve 238 closes and the maximum fluid flow of the fluid flows through the primary tube 231.

Once the primary tube 231 is found, due to the flowing fluid, the clamp 160 (and/or direct pressure) can then be applied to the primary tube 231 to stop the bleeding. Further, once clamped, the primary tube 231 may be ligated with sutures 262 to stop the bleeding.

If the primary tube 231 was properly ligated, the primary tube 231 should be occluded, and the bypass valve 238 should be fully open due to the back pressure created by the occluded primary tube 231 meeting the opening pressure of the bypass valve 238. The maximum fluid flow of the fluid flows through the exhaust tube 234 and fills the reservoir, indicating that the wound was properly ligated and occluded.

If the suture 262 was not properly applied, the primary tube 231 will still flow fluid indicating that the primary tube 231 was not properly occluded. This will create a marginal amount of back pressure in the tubing system 230. This back pressure will partially open the bypass valve 238 and a slow trickle of fluid flows through the exhaust tube 234 and fills the reservoir, providing an additional indicator that the wound was not properly packed and occluded.

Figure 14:
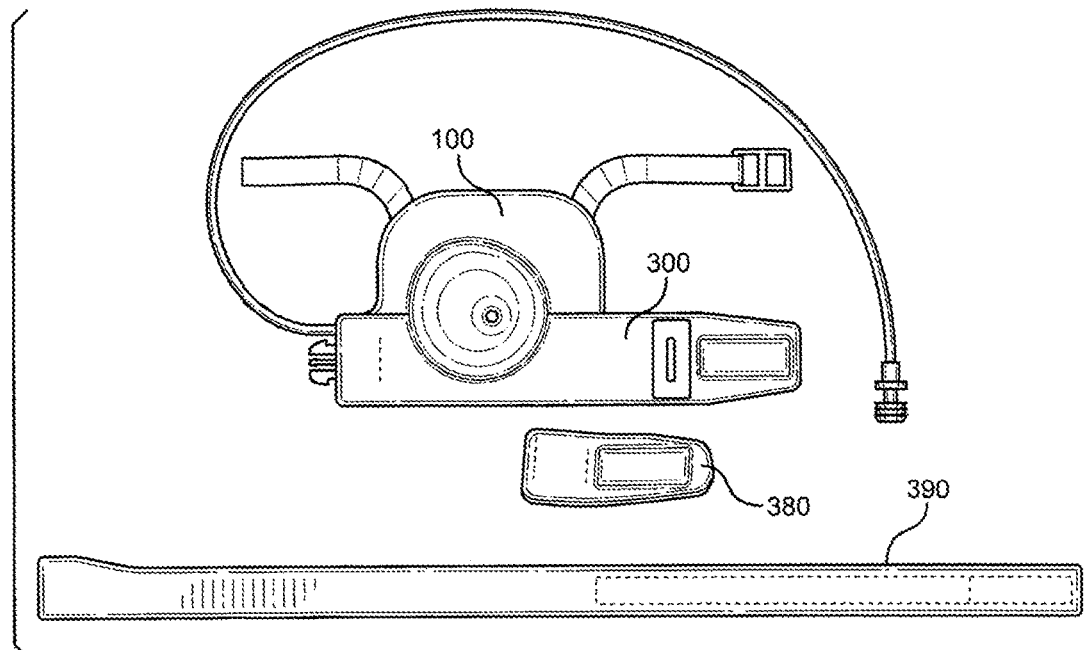
FIG. 14 is a front view of a multi-junctional bleeding simulator, with a neck strap and an extended strap, according to an alternate embodiment of the disclosure.
Figure 15:
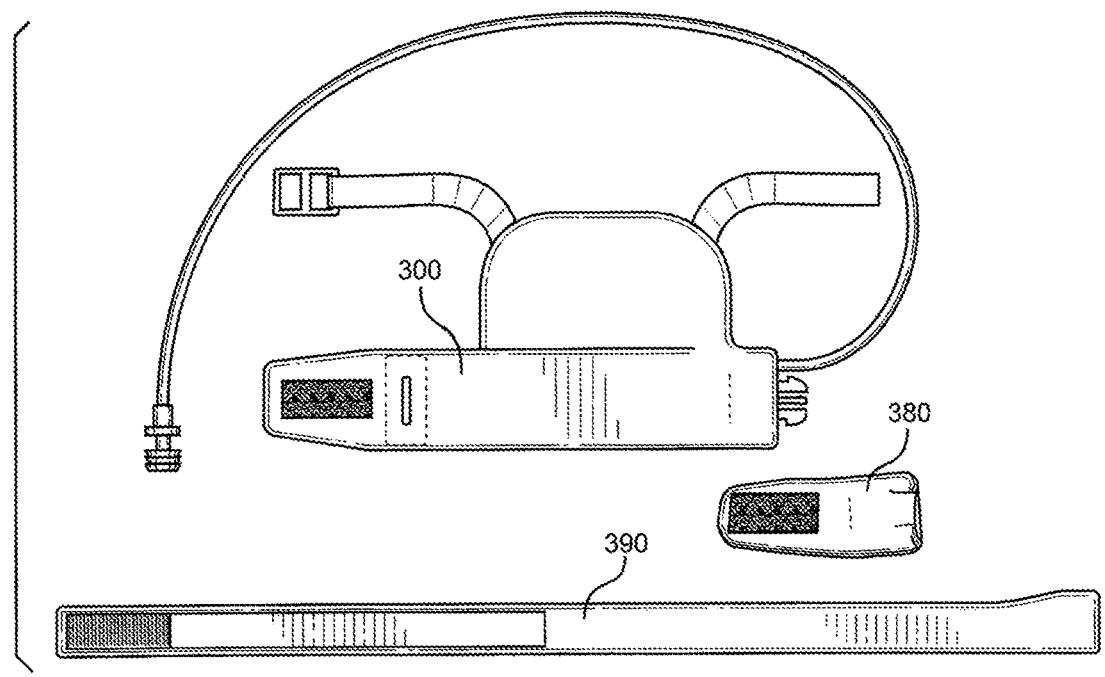
FIG. 15 is a back view of the multi-junctional bleeding simulator, with a neck strap and an extended strap, according to one embodiment of the disclosure.

Referring now to FIG. 14, in conjunction with FIG. 15, the multi-junctional bleeding simulator 100 is shown with a multi-junctional attachment unit 300. The multi-junctional attachment unit 300 includes a neck strap 380 and an extended strap 390. The multi-junctional attachment unit 300 with either the neck strap 380 or the extended strap 390 may provide the ability for the multi-junctional bleeding simulator 100 to be attached to several different areas of a live actor.

The multi-junctional attachment unit 300 with multi-junctional bleeding simulator 100 can be worn in one of three positions as follows: the neck junction, the axillary junction (armpit), and the inguinal junction (groin). In particular, the neck junction is just forward of the junction of the neck and the trunk of the body on both left and right sides. The axillary junction is the junction of the arm and flank around the armpit on both the left and right sides. The inguinal junction is the front side of the junction of the leg and the pelvis to the side of the genital on both left and right sides. The placement of the multi-junctional attachment unit 300 with multi-junctional bleeding simulator 100 at the neck junction may simulate a severed carotid artery, the placement at the axillary junction may simulate a severed axillary artery, and the placement at the inguinal junction may simulate a severed femoral artery, or any other blood vessel in the designated areas.

Figure 16:
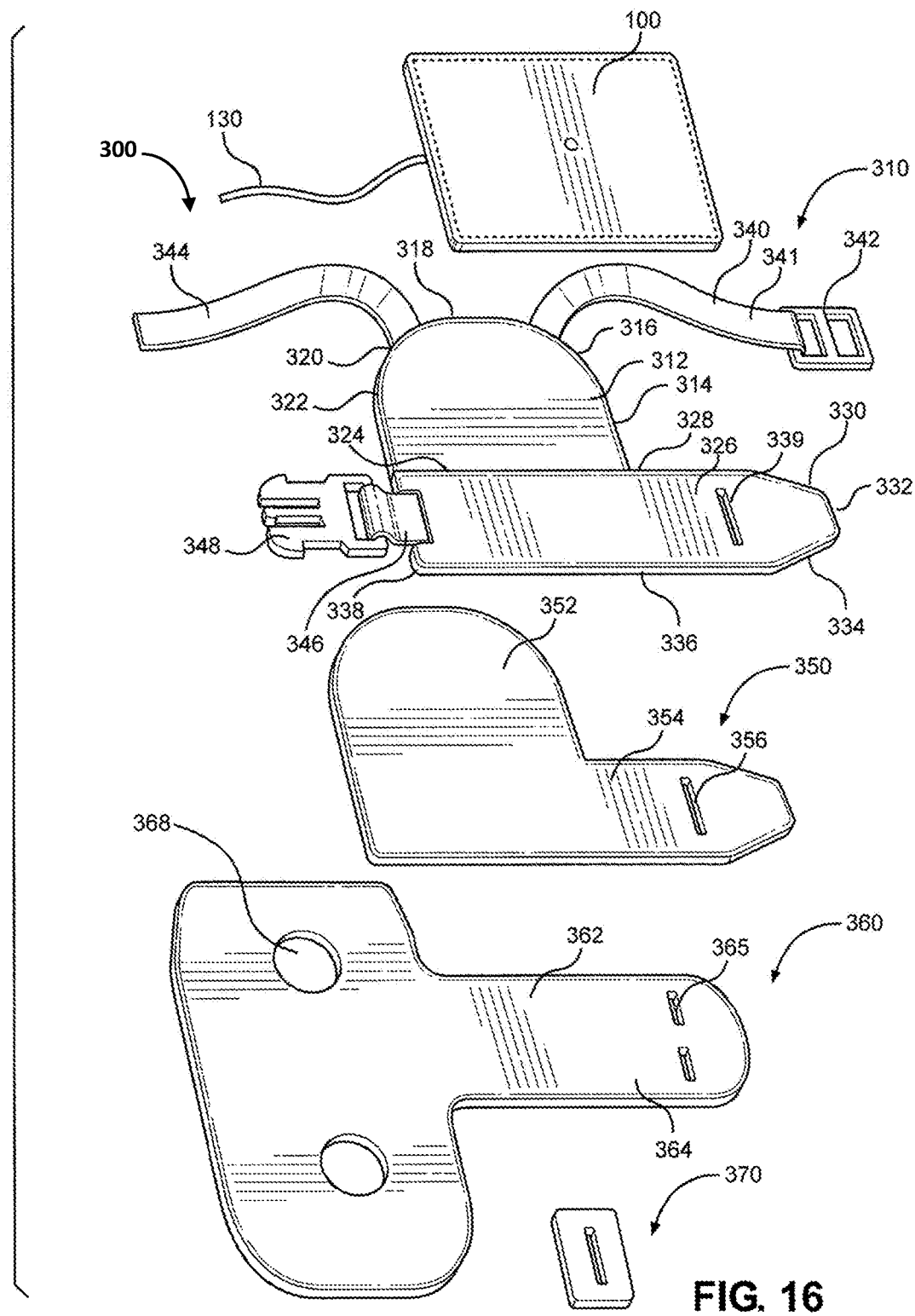
FIG. 16 is an exploded view of the multi-junctional bleeding simulator, according to one embodiment of the disclosure.

Referring now to FIG. 16, an exploded view of the multi-junctional attachment unit 300 is shown with the multi-junctional bleeding simulator 100. The use of the multi-junctional attachment unit 300 with the multi-junctional bleeding simulator 100 is not meant to be limiting and it is contemplated that the multi-junctional bleeding simulator 200 or any other embodiment of the disclosure may be used with the multi-junctional attachment unit 300.

According to one embodiment, and as shown, the multi-junctional attachment unit 300 may include a base protection layer 310, a padding layer 350, and a cover 360. The multi-junctional bleeding simulator 100 may be attached to the topside of the protection layer 310.

The base protection layer 310 may include an upper portion 312 and a lower portion 326. The upper portion 312 may have a right edge 314, a right curved edge 316, a top edge 318, a left curved edge 320, a left edge 322 and a bottom edge 324. The edges of the upper portion 312 may form a rough semi-circular shape. Adjacent the bottom edge 324 of the upper portion 312 is the lower portion 326. The lower portion 326 may have a top edge 328, a top-right tapered edge 330, a right edge 332, a bottom-right tapered edge 334, a bottom edge 336, and a left edge 338.

The upper portion 312 and the lower portion 326 may be made of ABS plastic with a neoprene coating that is puncture and cut resistant. According to one embodiment, the upper portion 312 and the lower portion 326 may be made of single sheet of ABS plastic with a score line along the bottom edge 324 of the upper portion and the top edge 328 of the lower portion to allow each portion to easily move independent from the other portion. This may provide the flexibility needed of the base protection layer 310 to adapt to several different parts of a live actor. It is also contemplated that the upper portion 312 and the lower portion 326 are separate pieces joined together with a flexible material or other methods to allow the upper portion 312 and the lower portion 326 to move independently from the other.

The base protection layer 310 may further include one or more fasteners. For example, the adjustable limb strap 340 may include a first strap 341 with a friction buckle 342 attached to the top edge 318 of the upper portion 312 and a second strap 344 attached to the left curved edge 320 of the upper portion. The placement of the limb strap 340 at the upper edges of the upper portion 312 allows the limb strap 340 to strap around the live actor's arm or leg depending on the orientation of the multi-junctional attachment unit 300.

Also for example, a male slide release buckle 348 may be attached to the left edge 338 of the lower portion 326 with an attachment strap 346. The male side release buckle 348 allows the attachment of the neck strap 380 or the extended strap 390 to the multi-junctional attachment unit 300. Formed into the lower portion 326 adjacent the top-right tapered edge 330 and bottom-right tapered edge 334 is a slot 339 formed to receive the extended strap 390.

The padding layer 350 may include an upper portion 352 and a lower portion 354 formed to have similar dimensions as the base protection layer 310. The padding layer 350 is pliable and does not need to have a score line, or similar, to allow the upper portion 352 to move independently of the lower portion 354. Formed in the lower portion is slot 356 corresponding to the location of slot 339. The padding layer 350 may be attached to the underside of the protection layer 310.

The cover 360 covers the assembly with the tube 130 protruding therefrom (e.g., out from the left edge 338). The cover 360 may include an upper portion 362, and a lower portion 364 that mirrors the upper portion 362. The upper portion 362 may include a slot 365 corresponding to the location of slots 356 and 339, and a cover opening 368 corresponding to the location of the opening 118 of the multi-junctional bleeding simulator 100. To illustrate, the upper portion 362 and the lower portion 364 may folded over each other along an axis from which they are mirrored so as to cover the rest of the assembly. A slot reinforcement 370 is attached to slots 365, 356, and 339.

Figure 17:
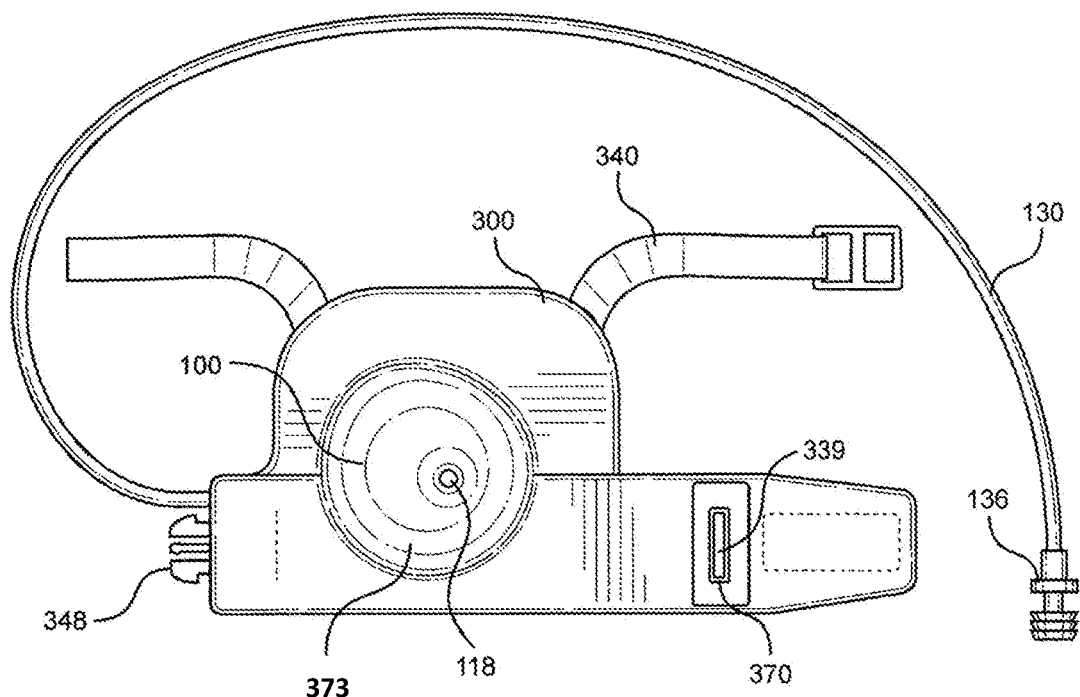
FIG. 17 is a front view of the multi-junctional bleeding simulator, according to one embodiment of the disclosure.

Referring now to FIG. 17, a top view of the multi-junctional attachment unit 300 with multi-junctional bleeding simulator 100 is shown. In particular, this would be an outward-facing view when the assembly is worn. As shown, the opening 118 of the multi-junctional bleeding simulator 100 simulating a puncture wound is exposed through the cover 360. Special effects 373, simulating human skin, is utilized to blend the cover 360 with the multi-junctional bleeding simulator 100 to provide a seamless transition between the multi-junctional bleeding simulator 100 and the cover 360. The limb strap 340 and the tube 130 protrude from the cover 360. The tube 130 includes an adapter 136 to connect to a blood pumping system to provide a flow of simulated blood to the wound. By wearing the multi-junctional attachment unit 300 with multi-junctional bleeding simulator 100 under clothing, a realistic bleeding puncture wound can be presented.

Figure 18:
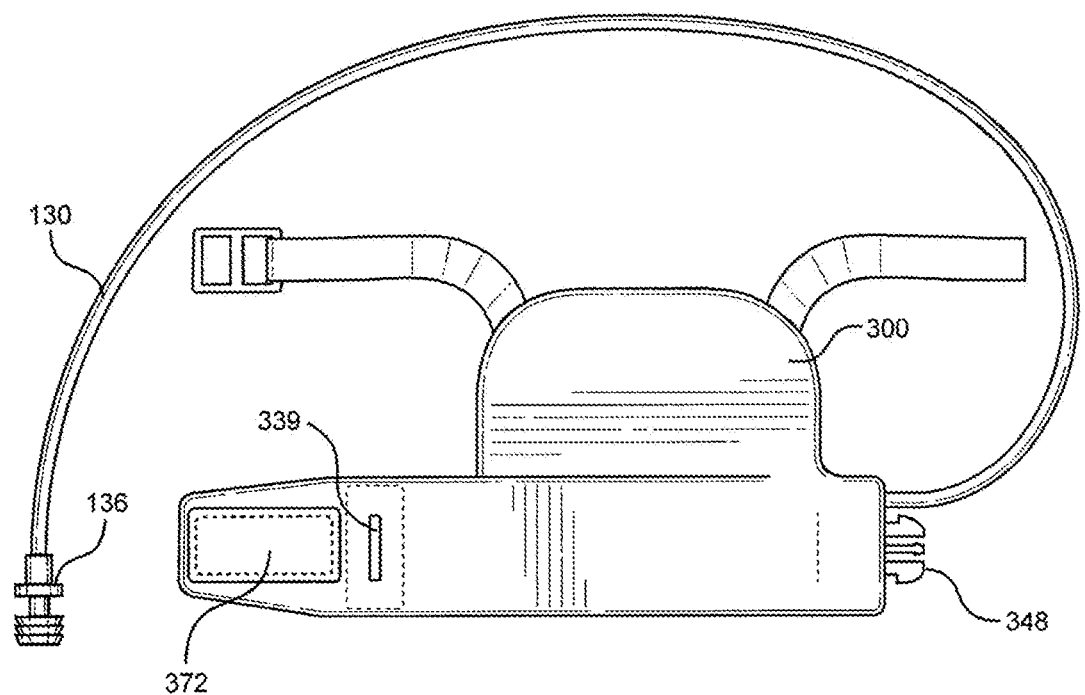
FIG. 18 is a back view of the multi-junctional bleeding simulator, according to one embodiment of the disclosure.

Referring now to FIG. 18, a bottom view of the multi-junctional attachment unit 300 with multi-junctional bleeding simulator 100 is shown. In particular, this would be an inward-facing view when the assembly is worn. A hook portion 372 is attached adjacent the slot 339. The hook portion 372 corresponds to a loop portion of the neck strap 380, and/or to the extended strap 390. In other words, the hook portion 372 is configured to couple to the neck strap 380, and/or to the extended strap 390 to accommodate being worn on the various body junctions of the wearer, as discussed above.

Figure 19:
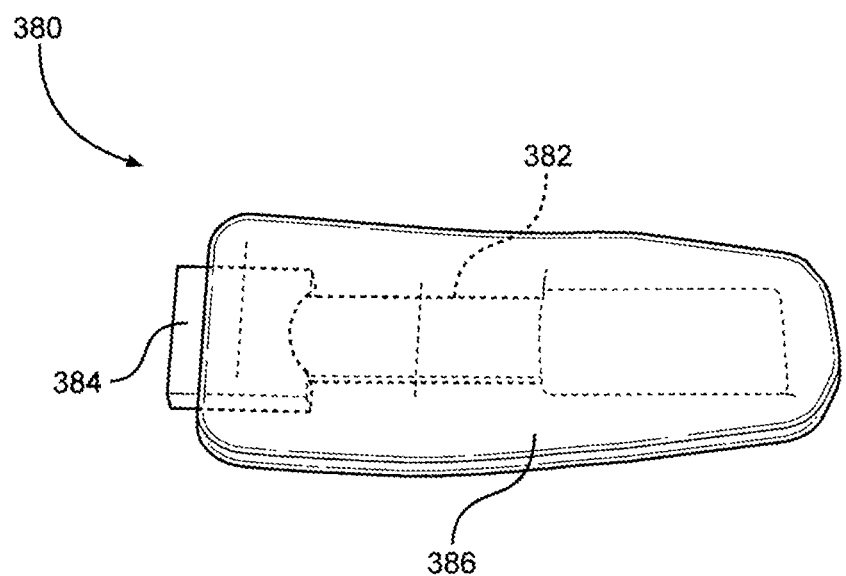
FIG. 19 is a front view of the neck strap of the multi-junctional bleeding simulator, according to one embodiment of the disclosure.
Figure 20:
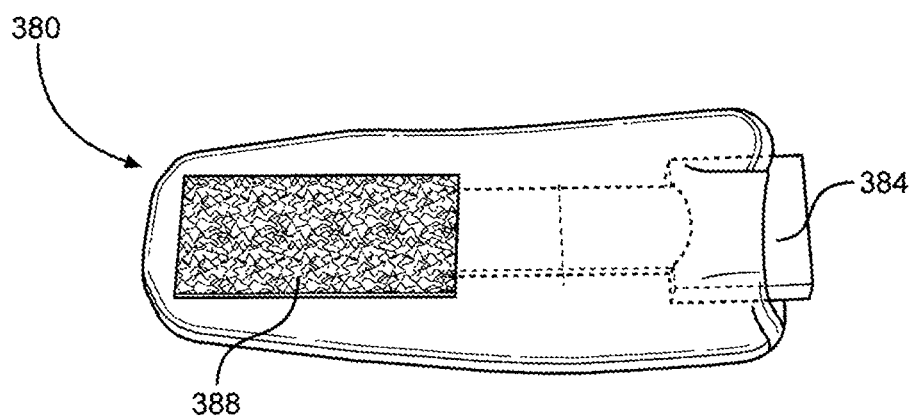
FIG. 20 is a back view of the neck strap of the multi-junctional bleeding simulator, according to one embodiment of the disclosure.

Referring now to FIG. 19 and FIG. 20, a front view and a back view of the neck strap 380 is shown, according to one embodiment of the disclosure, which is configured to couple to the hook portion 372 of the multi-junctional attachment unit 300, as discussed above. In this way, the assembly may be strapped to the user's neck when both are coupled together. As shown, the neck strap 380 may include a strap 382 (shown in dashed lines) with a female side release buckle 384 attached to one end. The strap 382 and the female side release buckle 384 are covered by a cover 386. Attached to the strap 382, over the cover 386, and opposite to the buckle 382, is a loop portion 388. The cover 386 is similar to the cover 360. As discussed throughout the disclosure, it is understood that many similar and/or equivalent embodiments are contemplated.

Figure 21:
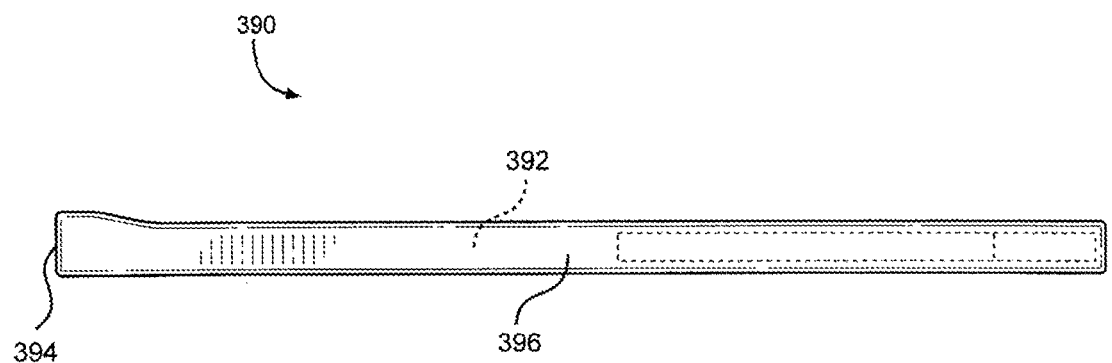
FIG. 21 is a front view of the extended strap of the multi-junctional bleeding simulator, according to one embodiment of the disclosure.
Figure 22:
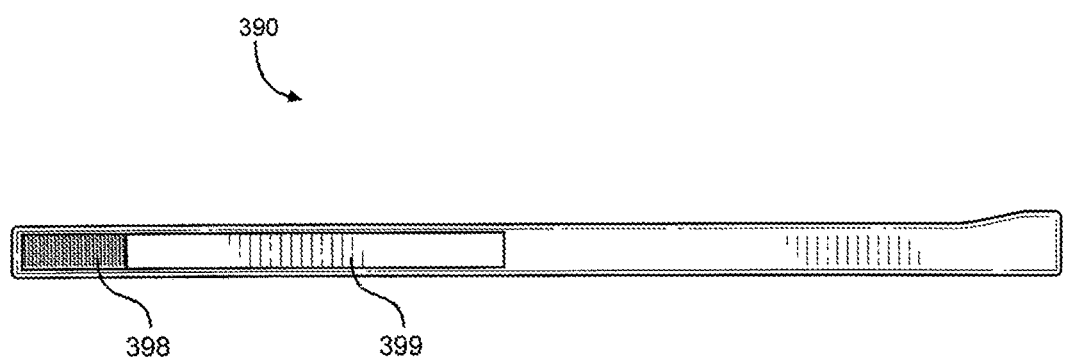
FIG. 22 is a back view of the extended strap of the multi-junctional bleeding simulator, according to one embodiment of the disclosure.
Figure 23:
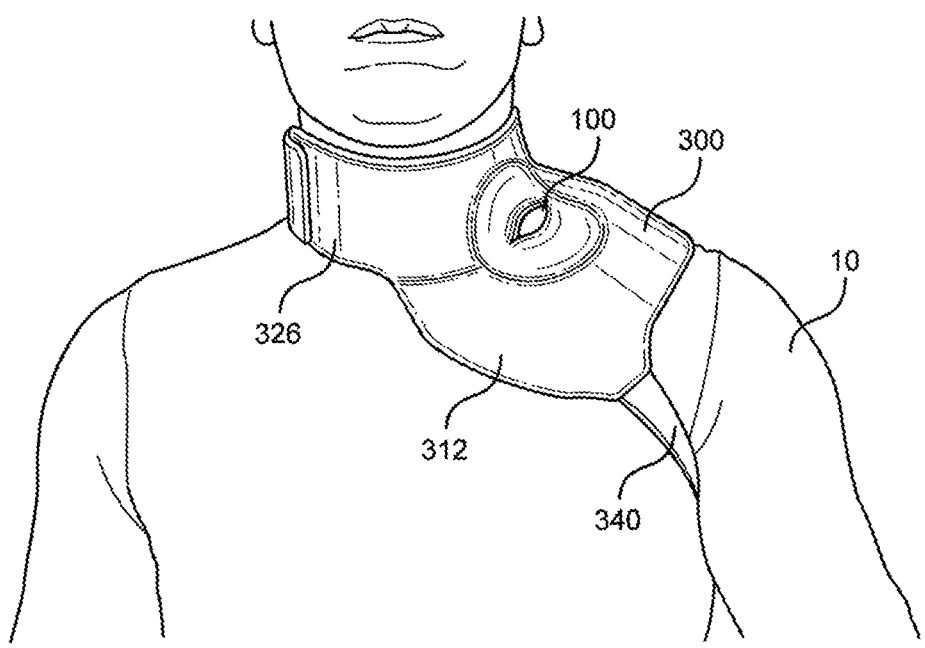
FIG. 23 is a front view of the multi-junctional bleeding simulator, attached to the neck junction of a live actor, according to one embodiment of the disclosure.
Figure 24:
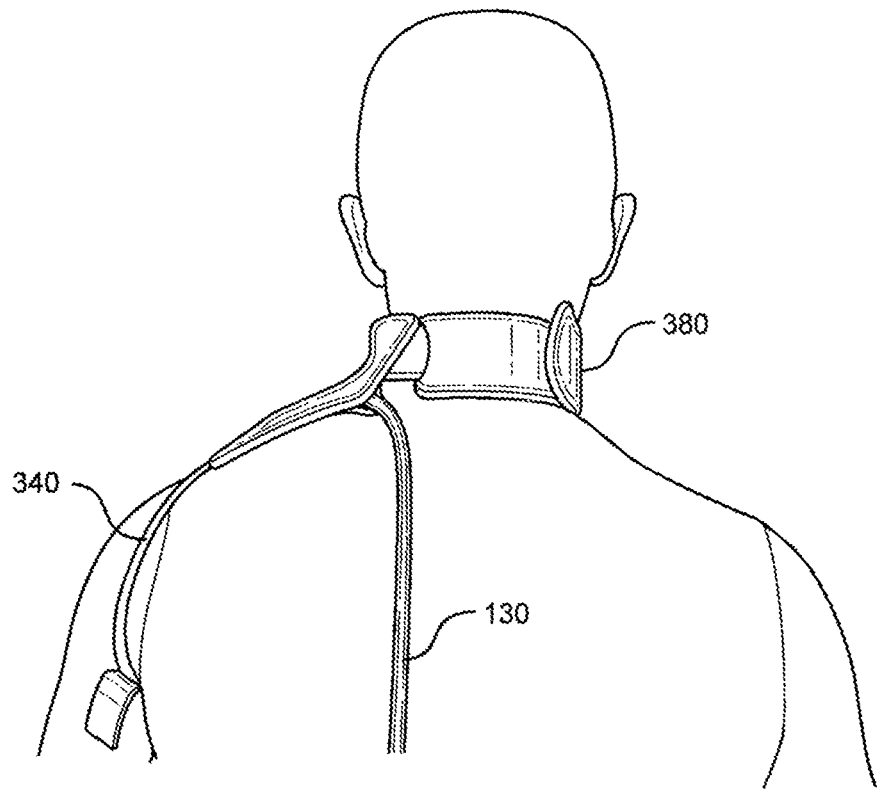
FIG. 24 is a back view of the multi-junctional bleeding simulator, attached to the neck junction of a live actor, according to one embodiment of the disclosure.
Figure 25:
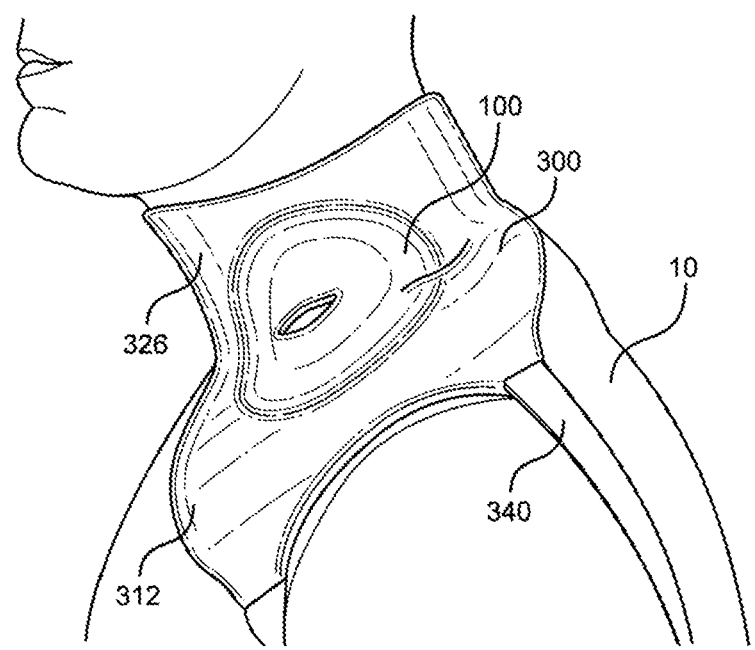
FIG. 25 is a left side view of the multi-junctional bleeding simulator, attached to the neck junction of a live actor, according to one embodiment of the disclosure.
Figure 26:
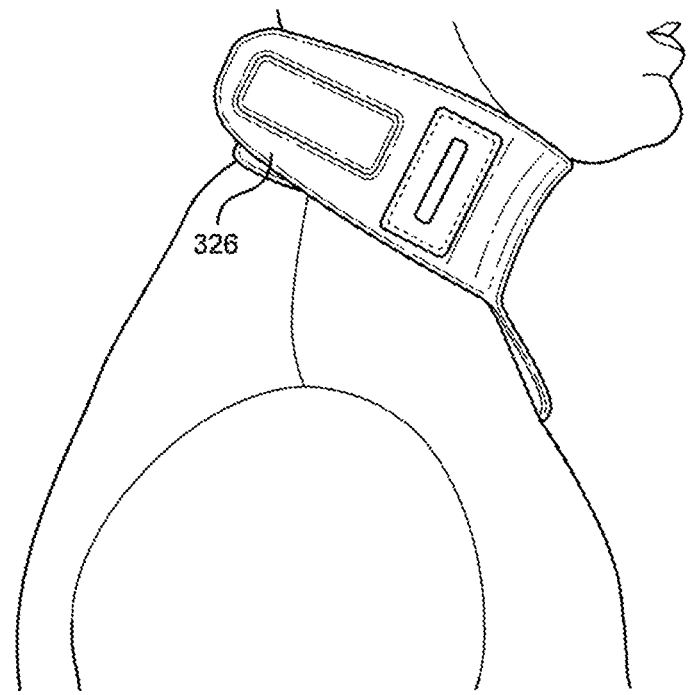
FIG. 26 is a right side view of the multi-junctional bleeding simulator, attached to the neck junction of a live actor, according to one embodiment of the disclosure.
Figure 27:
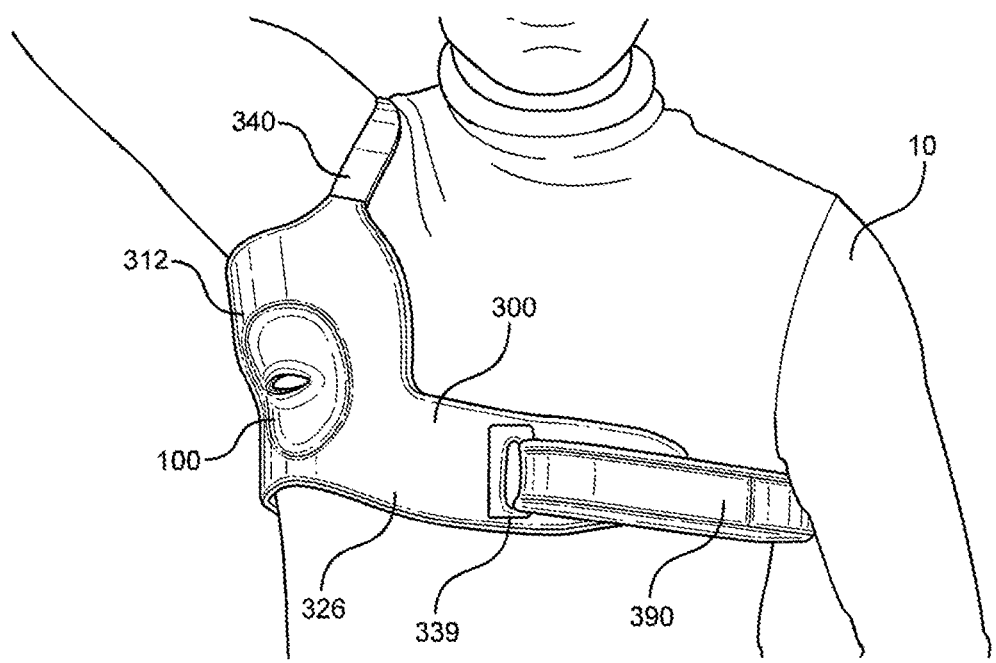
FIG. 27 is a front view of the multi-junctional bleeding simulator, attached to the axillary junction of a live actor, according to one embodiment of the disclosure.
Figure 28:
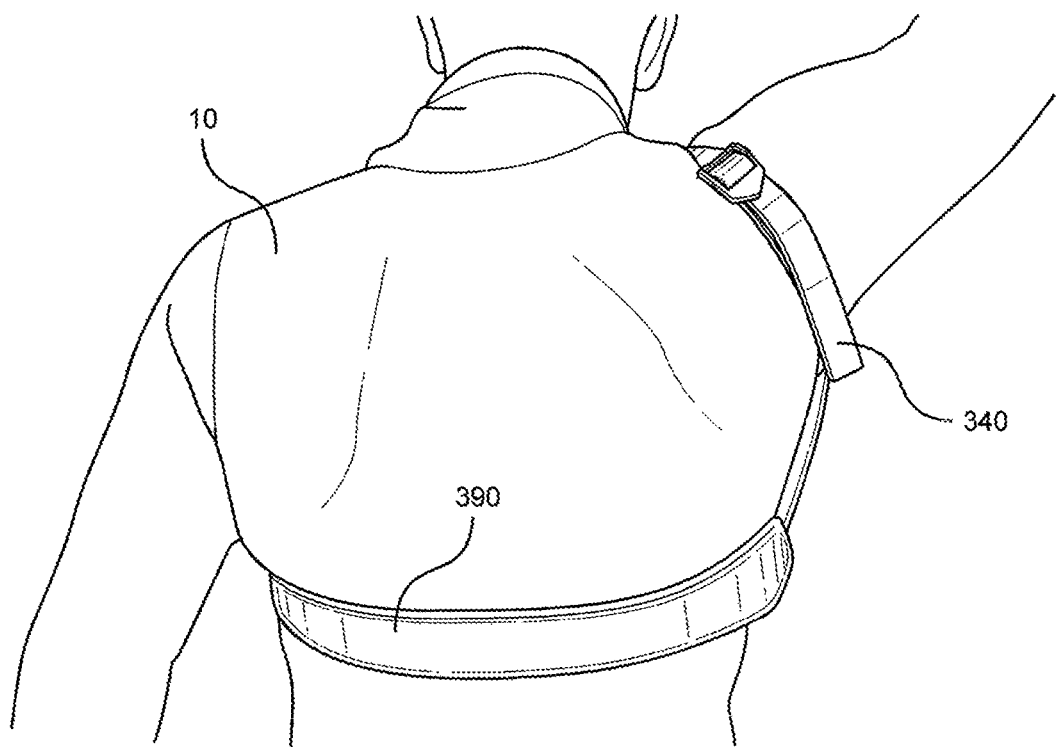
FIG. 28 is a back view of the multi-junctional bleeding simulator, attached to the axillary junction of a live actor, according to one embodiment of the disclosure.
Figure 29:
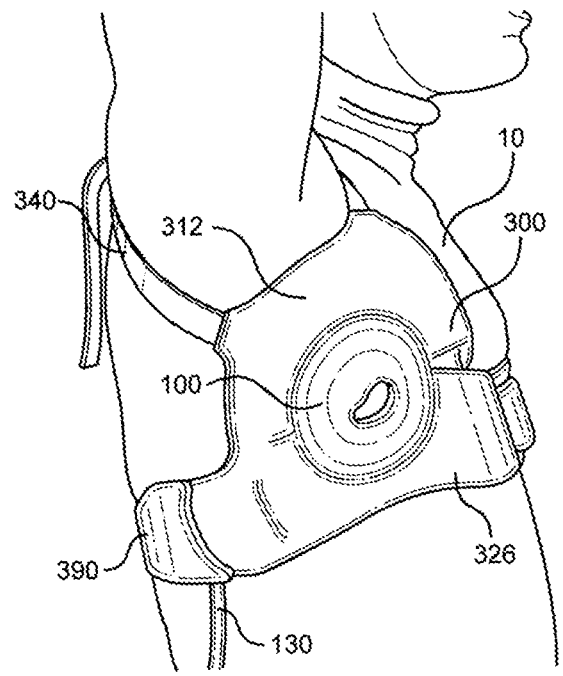
FIG. 29 is a right side view of the multi-junctional bleeding simulator, attached to the axillary junction of a live actor, according to one embodiment of the disclosure.
Figure 30:
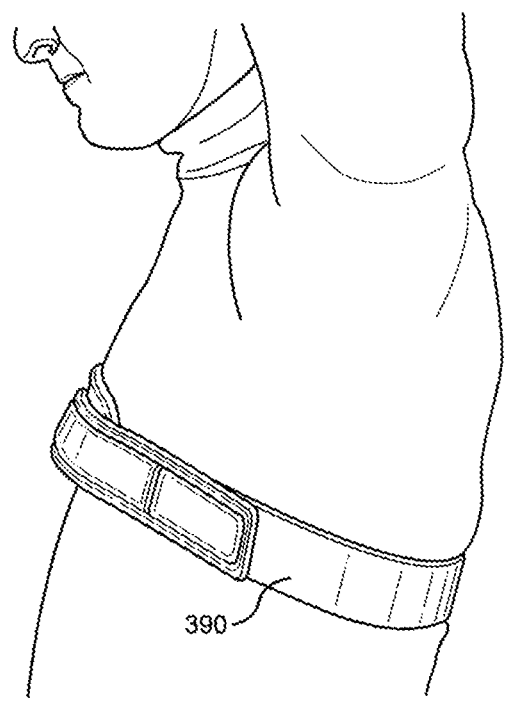
FIG. 30 is a left side view of the multi-junctional bleeding simulator, attached to the axillary junction of a live actor, according to one embodiment of the disclosure.
Figure 31:
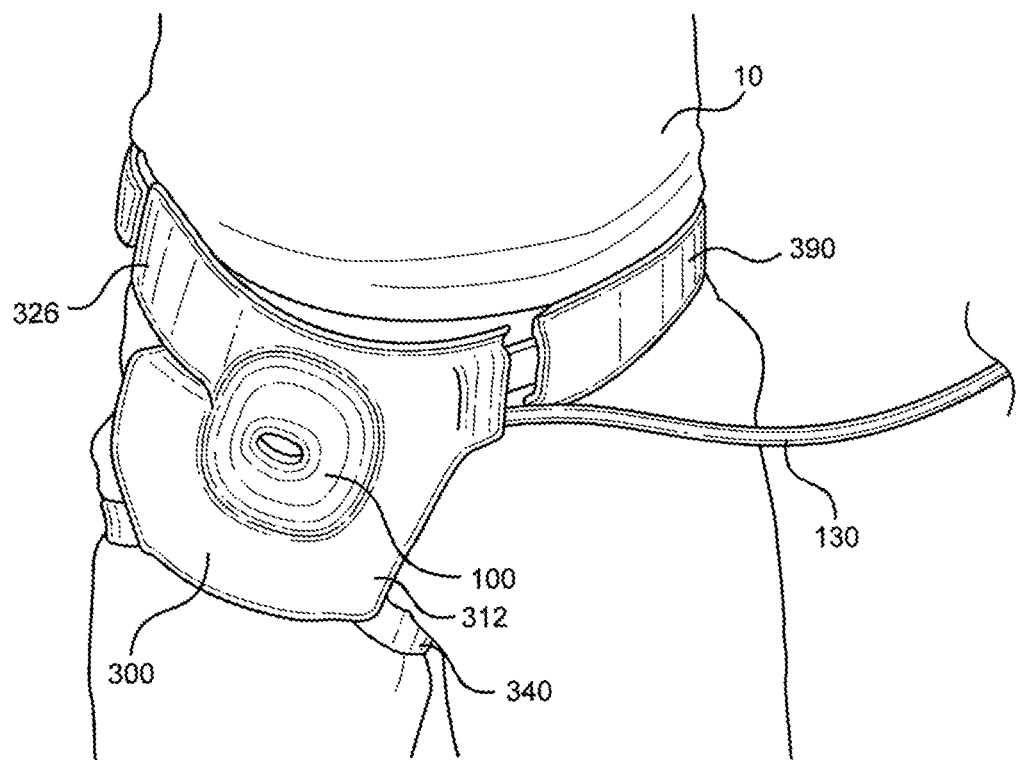
FIG. 31 is a front view of the multi-junctional bleeding simulator, attached to the inguinal junction of a live actor, according to one embodiment of the disclosure.
Figure 32:
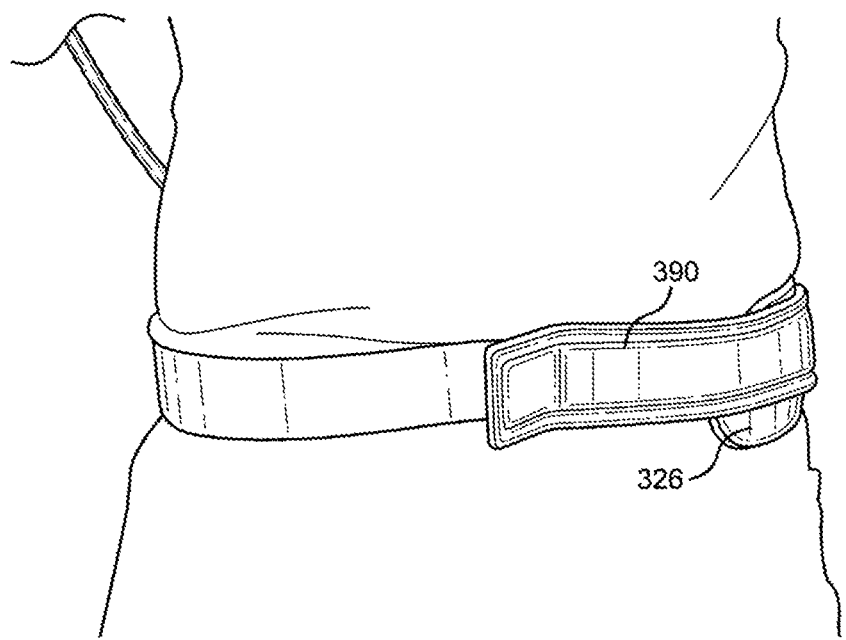
FIG. 32 is a back view of the multi-junctional bleeding simulator, attached to the inguinal junction of a live actor, according to one embodiment of the disclosure.
Figure 33:
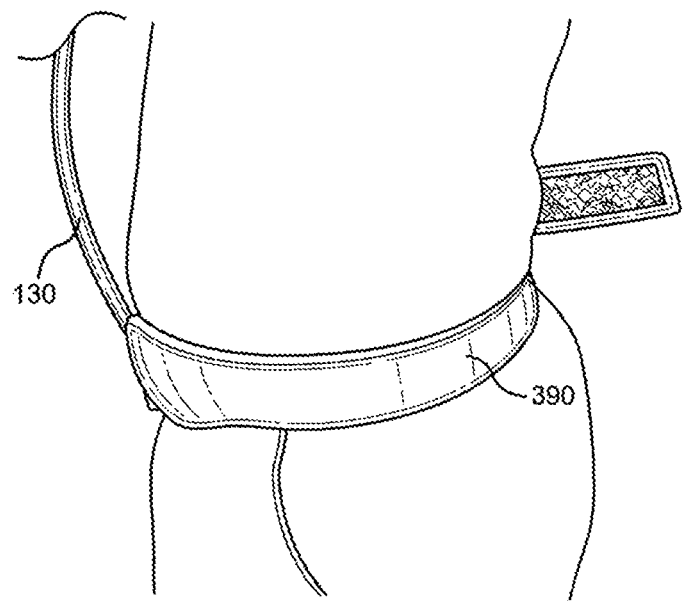
FIG. 33 is a left side view of the multi-junctional bleeding simulator, attached to the inguinal junction of a live actor, according to one embodiment of the disclosure.
Figure 34:
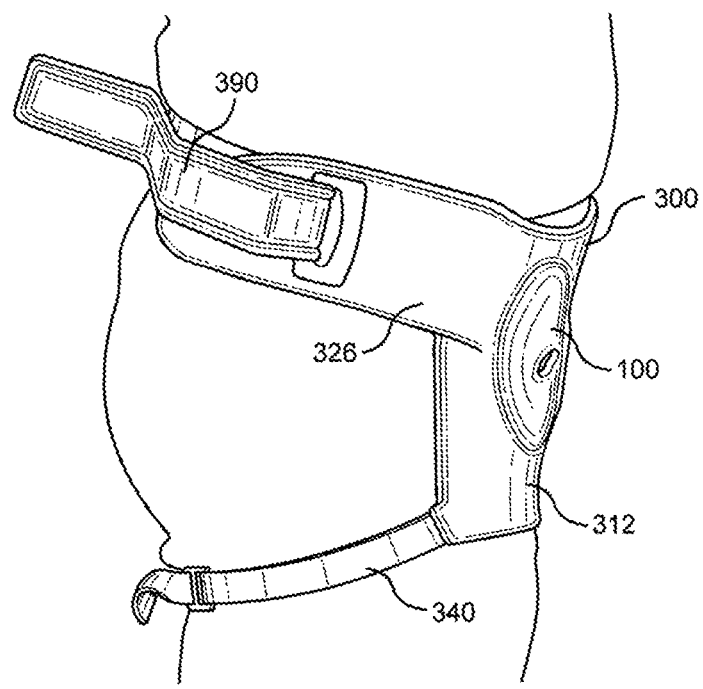
FIG. 34 is a right side view of the multi-junctional bleeding simulator, attached to the inguinal junction of a live actor.

Referring now to FIG. 21 and FIG. 22, a front view and a back view of the extended strap 390 is shown, according to one embodiment of the disclosure, which is configured to couple to the hook portion 372 of the multi-junctional attachment unit 300, as discussed above. In this way, the assembly may be strapped to the user's body (e.g., torso, leg, etc.) when both are coupled together. As shown, the extended strap 390 may include a strap 392 (shown in dashed lines) with a female side release buckle 394 attached to one end. The strap 392 and the female side release buckle 394 are covered by a cover 396. Attached to the strap 392, over the cover 396, and opposite to the buckle 392, are a loop portion 398 and a hook portion 399. The cover 396 is similar to the cover 360. The extended strap 390 is substantially longer in length than the neck strap 380. The extended strap is utilized to wrap around the torso of a live actor, whereas the neck strap 380 is utilized to wrap around the neck of a live actor. As discussed throughout the disclosure, it is understood that many similar and/or equivalent embodiments are contemplated.

Referring now to FIGS. 23-26, the multi-junctional attachment unit 300 with multi-junctional bleeding simulator 100 is attached at the neck junction of a live actor 10. The female side release buckle 384 of the neck strap 380 is attached to the male side release buckle 348 of the lower portion 326 of the multi-junctional attachment unit 300 (not shown). The neck strap 380 and the lower portion 326 wraps around the live actor's 10 neck, wherein the hook portion 372 of the lower portion hooks onto the loop portion 388 of the neck strap 380 (not shown). The limb strap 340 is connected to the live actor's 10 arm. This provides a secure attachment of the multi-junctional bleeding simulator 100 to the neck junction of the live actor 10. The silicone tube 130 is directed towards the back of the live actor 10 where it may be connected to a blood pumping system.

Referring now to FIGS. 27-30, the multi-junctional attachment unit 300 with attached multi-junctional bleeding simulator 100 is attached at the axillary junction of a live actor 10. The female side release buckle 394 of the extended strap 390 is attached to the male side release buckle 348 of the lower portion 326 of the multi-junctional attachment unit 300 (not shown). The extended strap 390 and the lower portion 326 wraps around the live actor's 10 torso, wherein the extended strap 390 is inserted through the slot 339 and the hook portion 399 hooks onto the loop portion 398. The limb strap 340 is connected to the of the live actor's 10 arm. This provides a secure attachment of the multi-junctional bleeding simulator 100 to the axillary junction of the live actor 10. The silicone tube 130 is directed towards the back of the live actor 10 where it may be connected to a blood pumping system.

Referring now to FIGS. 31-34, the multi-junctional attachment unit 300 with attached multi-junctional bleeding simulator 100 is attached at the inguinal junction of a live actor 10. The female side release buckle 394 of the extended strap 390 is attached to the male side release buckle 348 of the lower portion 326 of the multi-junctional attachment unit 300 (not shown). The extended strap 390 and the lower portion 326 wraps around the live actor's 10 torso, wherein the extended strap 390 is inserted through the slot 339 and the hook portion 399 hooks onto the loop portion 398. The limb strap 340 is connected to the of the live actor's 10 thigh. This provides a secure attachment of the multi-junctional bleeding simulator 100 to the inguinal junction of the live actor 10. The silicone tube 130 is directed towards the front of the live actor 10 where it may be connected to a blood pumping system.

While there have been shown what are presently considered to be preferred embodiments of the present disclosure, it will be apparent to those skilled in the art that various changes and modifications can be made herein without departing from the scope and spirit of the disclosure. Further, the above description of the various embodiments is provided to enable a person of ordinary skill in the art to make or use the subject matter of the disclosure. Various modifications to the embodiments will be readily apparent to those skilled in the art, and the generic principles defined herein may be applied to other variations without departing from the spirit or the scope of this disclosure. Thus, it is to be understood that the disclosure is not intended to be limited to the examples and designs described herein, which merely represent a presently preferred implementation of the disclosure, but that the disclosure is to be accorded the widest scope consistent with the principles and novel features disclosed herein. It is to be further understood that the scope of the present disclosure fully encompasses other embodiments that may become obvious to those skilled in the art.

The invention claimed is:

1. A wearable medical training device to be worn by a wearer for simulation of junctional bleeding of the wearer, the wearable medical training device comprising:
    a user interface configured to be worn by the wearer proximate a junction of the wearer when worn;
    a simulated hemorrhaging wound coupled to the user interface and configured to simulate a wound bleeding from said junction; and
    a blood feed coupled to the user interface and the simulated hemorrhage wound, the blood feed configured to communicate a simulated blood to the simulated hemorrhaging wound, and further configured to reduce or at least substantially stop a flow of the simulated blood to the simulated hemorrhaging wound upon proper performance of a hemorrhage control procedure; and
    wherein the blood feed includes a simulated blood vessel that is manually deformable, the blood feed further configured to reduce or stop the flow of the simulated blood upon performance of a ligation procedure on the simulated blood vessel;
    wherein the simulated hemorrhaging wound includes a bottom layer and a top layer attached together to form a simulated wound cavity therebetween, said top layer made to simulate human skin and including an opening configured to simulate a wound to said human skin;
    wherein the blood feed is further configured to reduce or stop the flow of the simulated blood upon performance of a compression procedure on or proximate the simulated blood vessel;
    wherein the bottom layer and the top layer are configured to rest against each other in a relaxed state, minimizing a volume of the simulated wound cavity, and further configured to deform away from each other upon application of a physical force, dynamically increasing said volume of the simulated wound cavity; and
    wherein the blood feed is further configured to reduce or stop the flow of the simulated blood upon compacting the simulated wound cavity with gauze.

2. The wearable medical training device of claim 1, wherein the blood feed is further configured
    to reduce the flow of the simulated blood upon application of pressure proximate the simulated blood vessel as part of the performance of the compression procedure on the simulated blood vessel,
    to resume the flow of the simulated blood upon removal of said pressure proximate the simulated blood vessel,
    to at least substantially stop the flow of the simulated blood upon performance of the ligation procedure on said simulated blood vessel, and
    to at least substantially stop the flow of the simulated blood upon compacting the simulated wound cavity with gauze.

3. The wearable medical training device of claim 1, wherein the user interface is further configured to be worn by the wearer proximate a neck junction of the wearer, repositioned and worn by the wearer proximate an axillary junction of the wearer, and further repositioned and worn by the wearer proximate an inguinal junction.

4. The wearable medical training device of claim 1, wherein the user interface includes
one or more reconfigurable straps configured to attach to the wearer in multiple locations,
a base protection layer configured to inhibit injury to the wearer from medical instruments during use of the wearable medical training device, and
a padding layer configured to increase stability and decrease movement of the wearable medical training device when worn.

5. A multi-junctional bleeding simulator to be worn by a wearer for simulation of junctional bleeding of the wearer, the multi-junctional bleeding simulator comprising:
a multi-junctional attachment unit configured to be worn by the wearer proximate a neck junction, repositioned and worn by the wearer proximate an axillary junction of the wearer, and further repositioned and worn by the wearer proximate an inguinal junction;
a simulated hemorrhage wound coupled to the multi-junctional attachment unit and configured to simulate a junctional bleeding wound and simulated bleeding from said junctional bleeding wound; and
a blood plumbing system coupled to the multi-junctional attachment unit and the simulated hemorrhage wound, the blood plumbing system configured to communicate a simulated blood to the simulated hemorrhage wound, and further configured to reduce or at least substantially stop a flow of the simulated blood to the simulated hemorrhage wound upon proper performance of a hemorrhage control procedure; and
wherein the simulated hemorrhaging wound further includes a bottom layer and a top layer attached together and forming a simulated wound cavity therebetween, said top layer made to simulate human skin and including an opening configured to simulate a wound to said human skin, the bottom layer and the top layer configured to rest against each other in a relaxed state, minimizing a volume of the simulated wound cavity, and further configured to be deformable away from each other upon application of a physical force, dynamically increasing said volume of the simulated wound cavity; and
wherein the blood plumbing system includes a simulated blood vessel that extends into the simulated wound cavity, said simulated blood vessel being manually deformable, said simulated blood vessel configured to expel the simulated blood into the simulated wound cavity.

6. The multi-junctional bleeding simulator of claim 5, wherein the multi-junctional attachment unit includes
one or more reconfigurable straps configured to attach to the wearer in multiple locations,
a base protection layer configured to prevent injury to the wearer from medical instruments during medical training, and
a padding layer configured to conform to the wearer and inhibit motion of the multi-junctional bleeding simulator during medical training, when worn.

7. The multi-junctional bleeding simulator of claim 6, wherein the multi-junctional attachment unit further includes a cover configured to substantially cover the base protection layer and the padding layer of the multi-junctional attachment unit, the simulated hemorrhage wound, and at least a portion of the blood plumbing system, the cover including a cover opening positioned and arranged to permit egress of the simulated bleeding from the junctional bleeding wound, and to provide sufficient access to the simulated hemorrhage wound for performance of the hemorrhage control procedure.

8. The multi-junctional bleeding simulator of claim 5, wherein the multi-junctional attachment unit includes a limb strap, a neck strap, and an extended strap,
the limb strap coupled to the multi-junctional attachment unit and configured to adjustably attach the multi-junctional attachment unit to a limb of the wearer,
the neck strap configured to removably couple to the multi-junctional attachment unit and to adjustably attach the multi-junctional attachment unit to a neck of the wearer, and
the extended strap configured to removably couple to the limb strap the multi-junctional attachment unit and to adjustably attach the multi-junctional attachment unit to a torso of the wearer.

9. The multi-junctional bleeding simulator of claim 5, wherein the opening of the top layer of the simulated hemorrhaging wound is configured to simulate a wound to the wearer including at least one of an abrasion, an excoriation, a hematoma, a laceration, an incision, a puncture wound, a contusion, a crushing injury, or a ballistic trauma.

10. The multi-junctional bleeding simulator of claim 5, wherein the simulated blood vessel extended into the simulated wound cavity is in misalignment with the opening of the top layer of the simulated hemorrhaging wound such that said opening of said top layer must be manipulated to access the simulated blood vessel.

11. The multi-junctional bleeding simulator of claim 5, wherein the simulated blood vessel is further configured
to reduce or at least substantially stop the simulating bleeding upon performance of a ligation procedure, and alternately,
to reduce or at least substantially stop the simulating bleeding upon performance of a compression procedure on or proximate the simulated blood vessel, and alternately,
to reduce or at least substantially stop the simulating bleeding upon compacting the simulated wound cavity with gauze.

12. The multi-junctional bleeding simulator of claim 5, wherein the blood plumbing system further includes a feed tube, an exhaust tube, and a bypass valve, the bypass valve fluidly coupling the feed tube to the simulated blood vessel and to the exhaust tube; and
wherein the flow of the simulated blood is normally plumbed to the simulated blood vessel, and the flow of the simulated blood is at least partially bypassed to the exhaust tube from the simulated blood vessel when a threshold backpressure is reached in the simulated blood vessel.

13. The multi-junctional bleeding simulator of claim 12, wherein the bypass valve has a fully open state triggered by a bypass backpressure, a partially open state triggered by a cracking backpressure, and a normally-closed state, the bypass backpressure corresponding to the hemorrhage control procedure being properly performed to stop bleeding, and the cracking backpressure corresponding to the hemorrhage control procedure being properly performed to slow bleeding.

14. A system for training hemorrhage control procedures on a wearer, the system comprising:

a pumping system including a supply of a simulated blood, a simulated blood pump configured to transmit the simulated blood, and a simulated blood reservoir configured to receive the simulated blood; and a multi-junctional bleeding simulator to be worn by the wearer for simulation of junctional bleeding of the wearer, the multi-junctional bleeding simulator including
- a multi-junctional attachment unit configured to be worn by the wearer proximate a neck junction, repositioned and worn by the wearer proximate an axillary junction of the wearer, and further repositioned and worn by the wearer proximate an inguinal junction,
- a simulated hemorrhage wound coupled to the multi-junctional attachment unit and configured to simulate a junctional bleeding wound and simulated bleeding from said junctional bleeding wound, and
- a blood plumbing system coupled to the multi-junctional attachment unit and the simulated hemorrhage wound, the blood plumbing system hydraulically coupled to the pumping system between the simulated blood pump and the simulated blood reservoir, blood plumbing system configured to communicate the simulated blood to at least one of the simulated hemorrhage wound and the simulated blood reservoir, the blood plumbing system further configured to reduce or at least substantially stop a flow of the simulated blood to the simulated hemorrhage wound upon proper performance of a hemorrhage control procedure; and wherein the simulated hemorrhage wound further includes a bottom layer and a top layer attached together and forming a simulated wound cavity therebetween, said top layer made to simulate human skin and including an opening configured to simulate a wound to said human skin, the bottom layer and the top layer configured to rest against each other in a relaxed state, minimizing a volume of the simulated wound cavity, and further configured to be deformable away from each other upon application of a physical force, dynamically increasing said volume of the simulated wound cavity;

wherein the blood plumbing system includes a simulated blood vessel that extends into the simulated wound cavity, said simulated blood vessel being manually deformable, said simulated blood vessel configured to expel the simulated blood into the simulated wound cavity; and wherein the simulated hemorrhage wound is further configured
- to reduce the simulated bleeding from the junctional bleeding wound upon application of pressure proximate the simulated blood vessel,
- to resume the simulated bleeding from the junctional bleeding wound upon removal of said pressure proximate the simulated blood vessel,
- to stop the simulated bleeding from the junctional bleeding wound upon performance of a ligation procedure on said simulated blood vessel, and
- to stop the simulated bleeding from the junctional bleeding wound upon performance of a compression procedure on the simulated blood vessel.

15. The system of claim 14, wherein the simulated blood reservoir is at least semi-transparent and configured to show that the simulated blood has flowed into the simulated blood reservoir indicating that the flow of the simulated blood through simulated blood vessel was restricted.

\* \* \* \* \*